(12) United States Patent
Liu et al.

(10) Patent No.: US 8,377,473 B2
(45) Date of Patent: *Feb. 19, 2013

(54) SLOW RELEASE MAGNESIUM COMPOSITION AND USES THEREOF

(75) Inventors: Guosong Liu, Palo Alto, CA (US); Fei Mao, Fremont, CA (US)

(73) Assignee: Magceutics, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,361

(22) Filed: Jul. 1, 2010

(65) Prior Publication Data

US 2011/0020443 A1 Jan. 27, 2011

Related U.S. Application Data

(60) Provisional application No. 61/222,420, filed on Jul. 1, 2009.

(51) Int. Cl.
*A61K 9/22* (2006.01)
*A61K 9/20* (2006.01)
*A61K 33/06* (2006.01)
*A61K 31/195* (2006.01)
*A61K 31/28* (2006.01)
*A01N 55/02* (2006.01)

(52) U.S. Cl. ......... 424/468; 424/464; 424/682; 420/402

(58) Field of Classification Search ............... 424/464
See application file for complete search history.

(56) References Cited

U.S. PATENT DOCUMENTS

| | | | |
|---|---|---|---|
| 4,985,256 A | 1/1991 | Glick | |
| 5,189,026 A | 2/1993 | Costa et al. | |
| 5,422,125 A | 6/1995 | Skyler et al. | |
| 5,549,789 A | 8/1996 | Atalla et al. | |
| 5,962,030 A | 10/1999 | Fine | |
| 6,294,583 B1 | 9/2001 | Fogel | |
| 6,313,170 B1 | 11/2001 | Yu et al. | |
| 6,403,129 B1 | 6/2002 | Clark et al. | |
| 6,498,247 B2 | 12/2002 | Evans et al. | |
| 6,548,687 B1 | 4/2003 | Yu et al. | |
| 6,727,288 B2 | 4/2004 | Yu et al. | |
| 6,835,398 B2 | 12/2004 | Cohen | |
| 8,142,803 B2 | 3/2012 | Liu et al. | |
| 8,163,301 B2 | 4/2012 | Liu et al. | |
| 8,178,118 B2 | 5/2012 | Liu et al. | |

(Continued)

FOREIGN PATENT DOCUMENTS

CN 1143464 A 2/1997
CN 1200366 A 12/1998

(Continued)

OTHER PUBLICATIONS

Sheng-Li et al., "Synthesis and Standard Enthalpy of Formation of Magnesium L-Threonate," Acta Phys.—Chim Sin, 2002, 18(11) 994-997.*

(Continued)

*Primary Examiner* — Daniel Sullivan
*Assistant Examiner* — Rachael E Bredefeld
(74) *Attorney, Agent, or Firm* — Wilson Sonsini Goodrich & Rosati

(57) ABSTRACT

The present invention provides compositions that contain magnesium and threonate, or a threonate precursor molecule, formulated for extended or modified release to provide physiological concentrations over a desired time period. The extended release or modified release form is particularly useful in providing Mg to a subject while avoiding adverse side effects such as diarrhea.

14 Claims, 6 Drawing Sheets

U.S. PATENT DOCUMENTS

| | | | |
|---|---|---|---|
| 8,178,132 B2 | 5/2012 | Liu et al. | |
| 8,178,133 B2 | 5/2012 | Liu et al. | |
| 2001/0010827 A1 | 8/2001 | Altura et al. | |
| 2004/0087608 A1 | 5/2004 | Okada et al. | |
| 2004/0091574 A1 | 5/2004 | Soe | |
| 2004/0146586 A1 | 7/2004 | Kaul et al. | |
| 2005/0214388 A1* | 9/2005 | Gorham et al. | 424/692 |
| 2005/0220865 A1 | 10/2005 | Koleng et al. | |
| 2006/0089335 A1 | 4/2006 | Liu et al. | |
| 2007/0098843 A1 | 5/2007 | Tomohira | |
| 2008/0269327 A1 | 10/2008 | Liu et al. | |
| 2012/0157533 A1 | 6/2012 | Liu et al. | |
| 2012/0171307 A1 | 7/2012 | Liu et al. | |

FOREIGN PATENT DOCUMENTS

| | | | |
|---|---|---|---|
| EP | 1038524 A1 | | 9/2000 |
| WO | WO 2005/049053 A1 | | 6/2005 |
| WO | WO2008/116226 | * | 9/2008 |

OTHER PUBLICATIONS

Iannelli et al., about.com Guide, Jul. 31, 2005, p. 1, Accessed Feb. 25, 2012.*

Fine, et al. Diagnosis of magnesium-induced diarrhea. N Engl J Med. Apr. 11, 1991;324(15):1012-7.

Fine, et al. Intestinal absorption of magnesium from food and supplements. J Clin Invest. Aug. 1991;88(2):396-402.

International search report dated Aug. 31, 2010 for PCT Application No. US10/40849.

Quamme, G. Recent developments in intestinal magnesium absorption. Curr Opin Gastroenterol. Mar. 2008;24(2):230-5.

Rude, et al. Renal tubular maximum for magnesium in normal, hyperparathyroid, and hypoparathyroid man. J Clin Endocrinol Metab. Dec. 1980;51(6):1425-31.

Altura, et al. Role of magnesium in patho-physiological processes and the clinical utility of magnesium ion selective electrodes. Scand J Clin Lab Invest Suppl. 1996;224:211-34.

Chuktow, J. G. Metabolism of magnesium in central nervous system. Relationship between concentrations of magnesium in cerebrospinal fluid and brain in magnesium deficiency. Neurology. Aug. 1974;24(8):780-7.

Cilliler, et al. Serum Magnesium Level and Clinical Deterioration in Alzheimer's Disease. Gerontology. Nov. 8, 2007;53(6):419-422.

Dekosky, et al. Synapse loss in frontal cortex biopsies in Alzheimer's disease: correlation with cognitive severity. Ann Neurol. May 1990;27(5):457-64.

Durlach, J. Magnesium depletion and pathogenesis of Alzheimer's disease. Magnes Res. Sep. 1990;3(3):217-8.

Eby, et al. Rapid recovery from major depression using magnesium treatment. Med Hypotheses. 2006;67(2):362-70.

El-Adawy, et al. Characteristics and composition of watermelon, pumpkin, and paprika seed oils and flours. J Agric Food Chem. Mar. 2001;49(3):1253-9.

European search report and research opinion dated Nov. 24, 2010 for Application No. 08732781.3.

Fromm, et al. Magnesium attenuates post-traumatic depression/anxiety following diffuse traumatic brain injury in rats. J Am Coll Nutr. Oct. 2004;23(5):529S-533S.

Gang, et al. Determination of constant-volume combustion energy for the compounds of L-threonic acid with Mg (II), Mn (II), Co (II) and Ni(II). Chem Mag. Mar. 1, 2003; 5(3): 22.

Gao, et al. FTIR Studies of L-threonic Acid and Its Metal Compounds. Spectroscopy and Spectral Analysis. Apr. 2003; 23(2):276-278. (in Chinese with English abstract).

Gao, et al. Preparation and Standard Enthalpy of Formation of Magnesium L-Threonate. Acta Phys. Chim Sin. 2002, 18(11): 994-997 (full English translation).

Goodman, et al. Goodman and Gilman's The Pharmacological Basis of Thereapeutics, 10th Ed. New York: McGraw-Hill Medical Publishing Division; 2001; p. 551.

Hocking, M. B. Handbook of Chemical Technology and Pollution Control. 3rd Ed. Academic Press. 2005; p. 540.

Huttenlocher, P. R. Synaptic density in human frontal cortex—developmental changes and effects of aging. Brain Res. Mar. 16, 1979;163(2):195-205.

International search report dated Aug. 29, 2008 for PCT Application No. US2008/58073.

Kapaki, et al. Zinc, Copper and Magnesium Concentration in Serum and CSF of Patients With Neurological Disorders. Acta Neurol Scand. 1989;79:373-378.

Landfield, et al. Chronically elevating plasma Mg2+ improves hippocampal frequency potentiation and reversal learning in aged and young rats. Brain Res. Nov. 19, 1984;322(1):167-71.

Liu, et al. Properties of synaptic transmission at single hippocampal synaptic boutons. Nature. Jun. 1, 1995;375(6530):404-8.

Liu, G. Local structural balance and functional interaction of excitatory and inhibitory synapses in hippocampal dendrites. Nat Neurosci. Apr. 2004;7(4):373-9.

Masliah, et al. The Synaptic Organization of the Neocortex in Alzheimer's Disease. Med Hypotheses. Oct. 1993;41(4):334-40.

Middleton, et al. Promising strategies for the prevention of dementia. Arch Neurol. Oct. 2009;66(10):1210-5.

Miquel, et al. Favorable effects of the antioxidants sodium and magnesium thiazolidine carboxylate on the vitality and life span of *Drosophila* and mice. Exp Gerontol. 1979;14(5):279-85.

Office Action issued Jul. 2, 2007, in connection with U.S. Appl. No. 10/965,451 (U.S. 2006-0089335 A1), under examination.

Renger, et al. A developmental switch in neurotransmitter flux enhances synaptic efficacy by affecting AMPA receptor activation. Neuron. Feb. 2001;29(2):469-84.

Scheff, et al. Synapse loss in the temporal lobe in Alzheimer's disease. Ann Neurol. Feb. 1993;33(2):190-9.

Schimid, et al. Hemodynamic effect of magnesium salts. Naunyn Schmiedebergs Arch Exp Pathol Pharmakol. 1955;224(5-6):426-33 (in German with the translation of the 1st page).

Shah, et al. Donezepil for dementia. J R Soc Med. Oct. 1997;90(10):531-2.

Slutsky, et al. Enhancement of learning and memory by elevating brain magnesium. Neuron. Jan. 28, 2010;65(2):165-77.

Slutsky, et al. Enhancement of synaptic plasticity through chronically reduced Ca2+ flux during uncorrelated activity. Neuron. Dec. 2, 2004;44(5):835-49.

Tang, et al. Genetic enhancement of learning and memory in mice. Nature. Sep. 2, 1999;401(6748):63-9.

Turner, et al. Magnesium gluconate offers no more protection than magnesium sulphate following diffuse traumatic brain injury in rats. J Am Coll Nutr. Oct. 2004;23(5):541S-544S.

Vacher, et al. GABA(B) receptors as potential therapeutic targets. Curr Drug Targets CNS Neurol Disord. Aug. 2003;2(4):248-59.

Wilson, et al. Synaptic reorganization in scaled networks of controlled size. J Neurosci. Dec. 12, 2007;27(50):13581-9.

* cited by examiner

SLOW RELEASE MAGNESIUM COMPOSITION AND USES THEREOF

RELATED APPLICATIONS

This application claims the benefit of U.S. Provisional Application No. 61/222,420, filed Jul. 1, 2009, which is incorporated by reference herein in its entirety.

BACKGROUND OF THE INVENTION

Magnesium is the fourth most abundant mineral in the human body and plays multiple roles in maintaining good health. At the molecular level, magnesium is a cofactor for over 300 enzymes responsible for some of the most important biological activities in mammals, including humans. In living cells, magnesium is involved in the homeostasis of other minerals, such as sodium, potassium and calcium, and the formation, transfer, storage and utilization of adenosine triphosphate (ATP), a principal source of energy in living cells. In the human body, magnesium is involved in the maintenance of normal muscle and nerve function, heart rhythm, bone strength, and immune system health. Magnesium is also involved in the regulation of blood sugar levels and the promotion of normal blood pressure.

Magnesium deficit has been associated with several diseases, including hypertension, atherosclerosis, arrhythmia, diabetes, and metabolic syndromes. In addition, magnesium deficit accelerates cell-aging processes (Killilea D W, Ames B N. Magnesium deficiency accelerates cellular senescence in cultured human fibroblasts. Proc Natl Acad Sci USA. 2008 Apr. 15; 105:5768-73). Magnesium is also important for brain function. For example, magnesium deficit is implicated in attention deficit hyperactivity disorder (Kozielec T, Starobrat-Hermelin B. Magnes Res. 1997 June; 10:143-8; Mousain-Bosc M, Roche M, Polge A, Pradal-Prat D, Rapin J, Bali J P. Magnes Res. 2006 March; 19:46-52), affective disorders (Murck H. Nutritional neuroscience. 2002 December; 5:375-89), Alzheimer's disease (Andrasi E, Pali N, Molnar Z, Kosel S. J Alzheimers Dis. 2005 August; 7:273-84; Cilliler A E, Ozturk S, Ozbakir S. Gerontology. 2007 Nov. 8; 53:419-22; Lemke M R. Biol Psychiatry. 1995 Mar. 1; 37:341-3), migraine (Ramadan N M, Halvorson H, Vande-Linde A, Levine S R, Helpern J A, Welch K M. Headache. 1989 October; 29:590-3; Facchinetti F, Sances G, Borella P, Genazzani A R, Nappi G. Magnesium prophylaxis of menstrual migraine: effects on intracellular magnesium. Headache. 1991 May; 31:298-301), and Autism (Martineau J, Barthelemy C, Garreau B, Lelord G. Biol Psychiatry. 1985 May; 20:467-78; Pfeiffer S I, Norton J, Nelson L, Shott S. J Autism Dev Disord. 1995 October; 25:481-93; Strambi M, Longini M, Hayek J, Berni S, Macucci F, Scalacci E, Vezzosi P., Biol Trace Elem Res. 2006 February; 109:97-104).

Recently, it has been found that elevation of extracellular magnesium leads to a significant enhancement of synaptic plasticity and synaptic density in cultured hippocampal neurons (Slutsky I, Sadeghpour S, Li B, Liu G. Neuron. 2004 Dec. 2; 44:835-49). The synaptic network is believed to be involved in organization of neural circuits during early development and in learning and memory processes. Indeed, in patients with Alzheimer's disease, there is a strong inverse correlation between the number of synapses and the degree of cognitive impairment (Terry R D, Masliah E, Salmon D P, Butters N, DeTeresa R, Hill R, Hansen L A, Katzman R. Ann Neurol. 1991 October; 30:572-80; Selkoe D J. Science. 2002 Oct. 25; 298:789-91). During normal aging, memory decline also correlates with synaptic loss (Terry R D, Masliah E, Salmon D P, Butters N, DeTeresa R, Hill R, Hansen L A, Katzman R. Ann Neurol. 1991 October; 30:572-80). Interestingly, brain magnesium contents in AD patients (Andrasi E, Pali N, Molnar Z, Kosel S. J Alzheimers Dis. 2005 August; 7:273-84; Cilliler A E, Ozturk S, Ozbakir S. Gerontology. 2007 Nov. 8; 53:419-22) are lower than normal subjects. Elevation of brain magnesium might be beneficial for prevention of synapse loss and amelioration of memory decline during aging and the pathological processes of AD.

Despite the important physiological role of magnesium, people may not consume enough magnesium in their diets. In a national sample of the United States, the mean value of daily magnesium between the ages of 20-30 is ~300 mg for white and ~250 mg for black males. This daily intake declines, at ages above 70 years, to ~200 mg as a result of reduced food consumption. On the other hand, the recommended daily allowance (RDA) for males is 420 mg/day. Therefore, it is likely that the majority of the American male population has magnesium deficit, particularly during aging. A similar degree of deficit also occurs in American female population (Ford E S, Mokdad A H. J. Nutr. 2003 September; 133:2879-82). Based on this study, most of the American population needs to supplement their diet with an additional ~200 mg/day of magnesium. Interestingly, magnesium contained in food provides relatively high absorption rate magnesium (~50%), which may suggest that ~100 mg/day magnesium remains needed to be absorbed into the body. In general, most commercially available magnesium preparations have a magnesium absorption rate <~40%. For example, magnesium oxide, which is perhaps the most widely used magnesium supplement, has a magnesium absorption rate of only about 4% (Firoz M, Graber M. Bioavailability of US commercial magnesium preparations. Magnes Res. 2001 December; 14:257-62)). The present invention provides controlled release magnesium compositions for use as a magnesium dietary supplement.

SUMMARY OF THE INVENTION

To supply the population with sufficient magnesium, a very high dose of magnesium supplement is required to reach the recommended daily allowance (RDA). For example, 4 grams of magnesium oxide would be required as an oral supplement. A slow release magnesium composition offers several advantages. Slow release avoids high concentration of magnesium in the gastrointestinal (GI) tract. Unabsorbed magnesium in the GI tract often leads to diarrhea. Slow release can avoid accumulation of unabsorbed magnesium and reduce such adverse effects. The present invention discloses such dosage forms and methods of use thereof.

In one aspect, the present invention provides an oral dosage form comprising magnesium (Mg) and threonate (T), wherein said threonate comprises one or more of a threonate salt or a threonate precursor, wherein said oral dosage form has an in vitro dissolution profile in a dissolution medium, and wherein said dissolution profile ranges between less than or equal to 5% in about 2 hours, less than 10% in about 4 hours, less than 40% in about 6 hours, greater than or equal to 60% in about 10 hours, and greater than or equal to 80% in about 12 hours as measured using a USP type II (paddle) dissolution system at 75 rpm, at a temperature of 37° C.

In some embodiments, the magnesium and threonate in said oral dose form is encapsulated in a tablet. In some embodiments, at least a portion of said magnesium (Mg) and threonate (T) is complexed in a salt form of $MgT_2$. In some embodiments, at least a portion of said magnesium (Mg) and threonate (T) is complexed in a salt form of $MgT_2$ present in an amount equal to at least about 20 mg of Mg by weight. In other embodiments, a molar ratio between said threonate (T) and said magnesium (Mg) is greater than or equal to about 0.1 to 2. In yet other embodiments, the threonate precursor comprises a threonic acid, a threonate ester, or a threonate lactone. In still other embodiments, said magnesium (Mg) is present in an amount greater than about 1% by weight. In further embodiments, said magnesium (Mg) is present in an amount greater than about 5% by weight, or in an amount greater than about 7% by weight.

In some embodiments, said magnesium (Mg) is complexed with an anion selected from the group consisting of chloride, taurinate, lactate, gluconate, citrate, malate, succinate, sulfate, propionate, hydroxide, oxide, orotate, phosphate, borate, salicylate, carbonate, bromide, stearate, an amino acid, butyrate, aspartate, ascorbate, picolinate, pantothenate, nicotinate, benzoate, phytate, caseinate, palmitate, pyruvate, and threonate. In other embodiments, the oral dosage form further comprises a metal ion selected from the group consisting of calcium, potassium, sodium, chromium, iron, selenium, zinc, manganese, molybdenum, vanadium, and lithium. In some other embodiments, the oral dosage form further comprises one or more antioxidant selected from the group consisting of resveratrol, ellagic acid, quercetin, lipoic acid and vitamin C.

In some embodiments, said dissolution profile ranges between less than 5% in about 2 hours, less than 10% in about 4 hours, less than 40% in about 6 hours, greater than or equal to 60% in about 10 hours, and greater than or equal to 80% in about 12 hours as measured using a USP type II (paddle) dissolution system at 75 rpm, at a temperature of 37° C. In some embodiments, the dissolution profile is zero order.

In some embodiments, at least 75% of said magnesium (Mg) and threonate (T) in said oral dose form is provided in a controlled release dosage form. In some embodiments, at least 95% or more of said magnesium (Mg) and threonate (T) in said oral dose form is provided in a controlled release dosage form. In some embodiments, 100% of said magnesium (Mg) and threonate (T) in said oral dose form is provided in a controlled release dosage form.

In some embodiments, the dissolution medium is a saline solution. In some embodiments, the oral dosage form further comprises a polymer binder mixed with the magnesium (Mg) and threonate (T). In some embodiments, the polymer comprises polyvinylpyrrolidone. In some embodiments, the oral dosage form further comprises a pharmaceutically acceptable amount of magnesium stearate. In some embodiments, the oral dosage form further comprises of one or more of polyvinylpyrrolidone, polyvinyl acetate, or propylene glycol.

In another aspect, the present invention provides an oral dosage form comprising between about 10 mg to 500 mg elemental magnesium (Mg), wherein said oral dosage form is a controlled release formulation, and wherein upon administering said oral dosage form to a Sprague-Dawley rat at a dosage of equal to or less than about 75 mg/kg/day yields an incidence of diarrhea of less than 20%. In some embodiments, the incidence of diarrhea is less than 20% when administered at a dosage of equal to or less than about 75 mg/kg/day for at least about 3 days. In some embodiments, the dosage form has a dissolution rate of magnesium about 40-80% within about 6 to 10 hours. In some embodiments, said oral dosage form provides for an incidence of diarrhea of less than 50% when administered at a dosage of equal to or less than about 130 mg/kg/day.

In another aspect, the present invention provides an oral dosage form comprising magnesium (Mg) and threonate (T), wherein said threonate comprises one or more of a threonate salt or a threonate precursor, wherein said oral dosage form is effective in increasing the life span of a subject on a high calorie diet. In some embodiments, administering said oral dosage form to a subject on a high calorie diet yields a protective effect such that said subject's life span is comparable to an average life span of a subject having a median weight. In some embodiments, said oral dosage form is administered to a human subject at a dose between about 1 mg elemental magnesium/kg/day to about 16 mg elemental magnesium/kg/day. In some embodiments, the oral dosage form increases survival rate by at least about 40% in subjects who are on a high calorie diet for at least about 60 weeks.

In another aspect, the present invention provides an oral dosage form comprising magnesium (Mg) and threonate (T), wherein said threonate comprises one or more of a threonate salt or a threonate precursor, wherein administering said oral dosage form to a subject provides protection against adverse effects of a high calorie diet in said subject. The adverse effects can include but are not limited to artherosclerosis, heart disease, myocardial infarction, stroke, thromboembolism, metabolic syndrome, and diabetes. In some embodiments, said oral dosage form is administered to a human subject at a dose between about 1 mg elemental magnesium/kg/day to about 16 mg elemental magnesium/kg/day. In some embodiments, the oral dosage form increases survival rate by at least about 40% in subjects who are on a high calorie diet for at least about 60 weeks.

In another aspect, the present invention provides an oral dosage form comprising magnesium (Mg) and threonate (T), wherein said threonate comprises one or more of a threonate salt or a threonate precursor, wherein said oral dosage form is readily absorbed or retained upon administering said oral dosage form to a subject at least about 50% of said administered magnesium is absorbed in said subject, or that at least about 30% of the magnesium administered to the subject is retained over a period of at least two days when said oral dosage form is administered at a dose of about 20 mg/kg/day or higher.

In some embodiments, the subject is a Sprague-Dawley rat. In some embodiments, more than about 60% of said administered magnesium is absorbed in said subject. In some embodiments, more than about 40% of said administered magnesium is retained over a period of at least two days when said oral dosage form is administered at a dose of about 20 mg/kg/day or higher. In some embodiments, the oral dosage form exhibits a dose-proportional increase in absorbed magnesium when administered to a subject in an amount between about 20 mg/kg/day and about 80 mg/kg/day.

In some embodiments, the oral dosage forms of the present invention comprise magnesium (Mg) and threonate (T), wherein said threonate comprises one or more of a threonate salt or a threonate precursor, and wherein the oral dosage form when administered to the subject provides an increased concentration of magnesium in a cerebral spinal fluid of the subject, wherein said increased concentration of magnesium in said cerebral spinal fluid of the subject ranges between about a 5% increase to about a 10% increase after about 10 days administering said oral dosage form to said subject as compared to a baseline magnesium concentration in the absence of administering magnesium.

In another aspect, the present invention provides a method of treating a condition related to magnesium deficiency comprising administering to a subject in need thereof an oral dosage form disclosed herein. In some embodiments, the condition is selected from the group consisting of a neurological disorder, a cardiovascular disorder, and a metabolic disorder.

In yet another aspect, the present invention provides a method of elevating magnesium in a central nervous system of a subject in need thereof comprising administering to said subject an oral dosage form provided by the invention.

In yet another aspect, the present invention provides a method of maintaining a high calorie diet without a substantial risk of high calorie related adverse effect, comprising administering to a subject in need thereof an oral dosage form provided by the invention.

In still another aspect, the present invention provides a method of supplementing magnesium in a subject in need thereof, comprising administering an oral dosage form provided by the invention to said subject at least once a day.

In yet still another aspect, the present invention provides a method of supplementing magnesium in a subject in need thereof, comprising administering an oral dosage form provided by the invention to said subject at least twice a day for a period of 1 month or longer.

The present invention also provides a method of making an oral dosage form as described above, comprising mixing a powder comprising magnesium (Mg) and threonate (T), both of which being present in a salt form, with a polymer in an amount sufficient to create particles comprising the magnesium (Mg), the threonate (T), and the polymer, wherein said particles are of a size sufficient to be retained by a 12 mesh sieve. In some embodiments, the method further comprises filtering said particles to remove un-bound threonate using the 12 mesh sieve; drying the particles; adding a pharmaceutically acceptable amount of lubricant to said particles; compressing the particles into one or more pills of size between about 100 mg and about 2000 mg; and coating said one or more pills with a polymer coating comprising one or more of polyvinylpyrrolidone, polyvinyl acetate, or propylene glycol.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A illustrates the relationship between magnesium (Mg) intake and the absorbed amount of magnesium for magnesium threonate (MgT) and $MgCl_2$. The absorption rate was estimated by linear regression. FIG. 2B illustrates the absorption rate of different magnesium preparations displayed as a percentage. FIG. 2C illustrates the relationship between absorbed magnesium and magnesium excreted in the urine. The excretion rate was estimated by linear regression. FIG. 2D illustrates the excretion rate of different magnesium preparations displayed as a percentage. FIG. 2E illustrates the relationship between magnesium intake and its retention in the body. The retention rate was estimated by linear regression. FIG. 2F illustrates the retention rate of different magnesium preparations displayed as a percentage.

DETAILED DESCRIPTION OF THE INVENTION

I. Controlled Release Oral Dosage Forms

Figure 1:
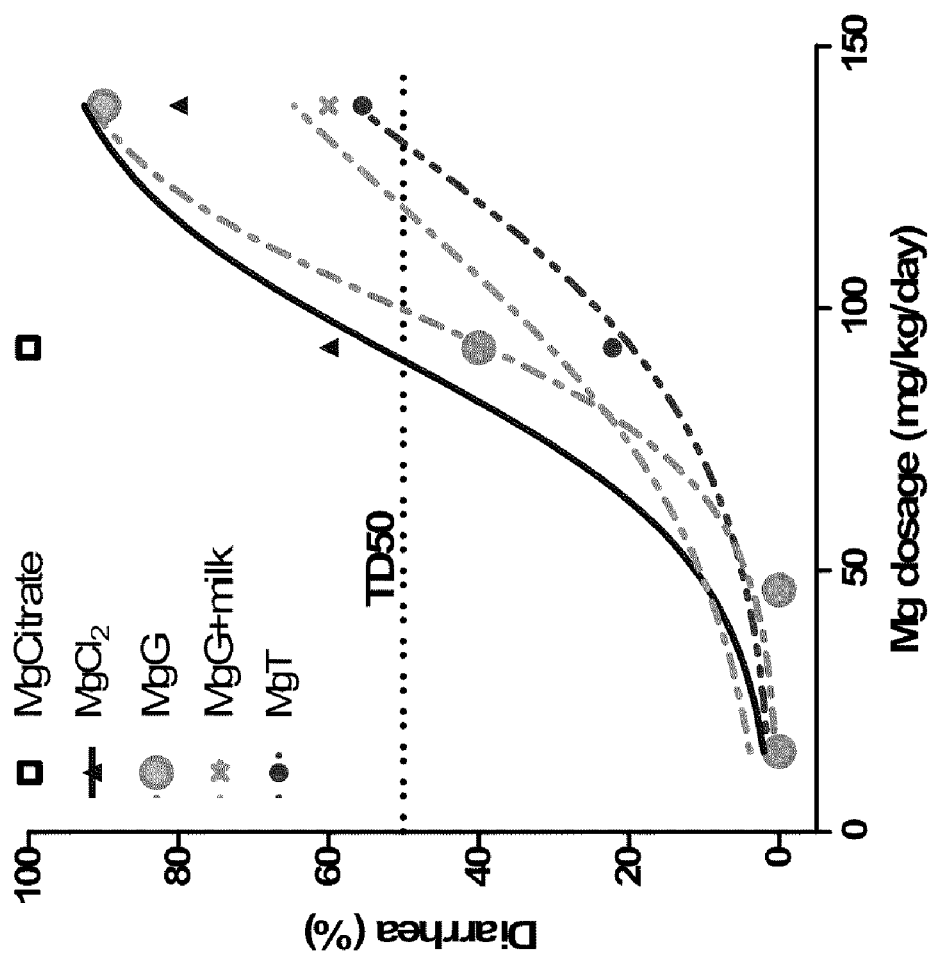
FIG. 1 illustrates a plot of the incidence of diarrhea in rats provided different magnesium preparations. The y-axis is the incidence of diarrhea and the x-axis is the dosage of elemental magnesium per kg per day. The magnesium compounds were magnesium citrate (MgCltrate); magnesium chloride ($MgCl_2$); magnesium gluconate (MgG); magnesium gluconate in milk (MgG+milk); and magnesium threonate (MgT).

The present invention provides compositions that contain magnesium and threonate, or a threonate precursor molecule, formulated for extended or modified release to provide a serum or plasma concentration over a desired time period that is high enough to be physiologically effective but at a rate low enough so as to avoid adverse events associated with high levels of magnesium. Adverse effects that would otherwise be associated with high Mg content include diarrhea. Controlled release of the magnesium is desirable for reducing and delaying the peak plasma level while maintaining bioavailability. Physiologically effective levels are therefore achieved while minimizing side-effects that can be associated with immediate release formulations. Furthermore, as a result of the delay in the time to obtain peak serum or plasma level and the extended period of time at the therapeutically effective serum or plasma level, the dosage frequency is reduced to, for example, once or twice daily dosage, thereby improving subject compliance and adherence. For example, side effects including diarrhea associated with the administration of magnesium may be lessened in severity and frequency through the use of controlled-release formulations that increase the time to maximum concentration in the body, thereby reducing the change in concentration of the magnesium over time. Reducing the concentration change also reduces the concentration of the active ingredient at its maximum time point and provides a more constant amount of magnesium to the subject being treated over a given period of time, which can further enable increased dosages for appropriate indications.

Controlled release within the scope of this invention can be taken to mean any one of a number of extended release dosage forms. Non-limiting examples of extended release dosage forms are described in Heaton et al. U.S. Patent Application Pub. No. 2005/0129762 and Edgren et al. U.S. Patent Application Pub. No. 2007/0128279, which are herein incorporated by reference. Time-release formulations are known in the art, some of which are described in Sawada et al. U.S. Patent Application Pub. No. 2006/0292221, herein incorporated by reference. The following terms may be considered to be substantially equivalent to controlled release for the purposes of the present invention: modified release, continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.). The various controlled release technologies cover a very broad spectrum of dosage forms. Controlled release technologies include, but are not limited to, physical systems and chemical systems.

A composition, kit, and/or a method described herein may be useful for purposes described herein, such as maintaining, enhancing, and/or improving health, nutrition, and/or another condition of a subject, and/or cognitive, learning, and/or memory function, for example, such as magnesium deficiency, mild cognitive impairment (MCI), Alzheimer's disease (AD), attention deficit hyperactivity disorder (ADHD), amyotrophic lateral sclerosis (ALS) or Lou Gehrig's disease, Parkinson's disease, Schizophrenia, diabetes, migraine, anxiety, mood, and hypertension, merely by way of example.

The compositions of the present invention can be formulated in slow release or sustained release forms, whereby a relatively consistent level of the magnesium threonate is provided over an extended period. In some embodiments, a magnesium counter-ion composition and/or other therapeutic agents may be administered jointly or separately by using a controlled release dosage form. In one embodiment, the present invention provides an oral dosage form comprising magnesium (Mg) and threonate (T), wherein said threonate comprises one or more of a threonate salt or a threonate precursor, wherein said oral dosage form has an in vitro dissolution profile in a dissolution medium, and wherein said dissolution profile ranges between less than or equal to 5% in about 2 hours, less than 10% in about 4 hours, less than 40% in about 6 hours, greater than or equal to 60% in about 10 hours, and greater than or equal to 80% in about 12 hours as measured using a USP type II (paddle) dissolution system at 75 rpm, at a temperature of 37° C. In another embodiment, the dissolution profile ranges between less than 5% in about 2 hours, less than 10% in about 4 hours, less than 40% in about 6 hours, greater than or equal to 60% in about 10 hours, and greater than or equal to 80% in about 12 hours as measured using a USP type II (paddle) dissolution system at 75 rpm, at a temperature of 37° C. In another embodiment, the dissolution profile ranges between less than 5% in about 2 hours, less than 10% in about 4 hours, less than 40% in about 6 hours, greater than or equal to 60% in about 10 hours, and greater than or equal to 80% in about 12 hours as measured using a USP type II (paddle) dissolution system at 75 rpm, at a temperature of 37° C. In some embodiments of the oral dosage forms as described herein, said magnesium and threonate is encapsulated in a tablet.

In some embodiments, at least 75% of said magnesium (Mg) and threonate (T) in the controlled release oral dosage forms of the present invention is provided in a controlled release dosage form. In some embodiments, at least 95% of said magnesium (Mg) and threonate (T) in the controlled release oral dosage forms is provided in a controlled release dosage form. In some embodiments, 100% of said magnesium (Mg) and threonate (T) in said oral dose form is provided in a controlled release dosage form. In some embodiments, the dissolution medium is a saline solution. In some embodiments, the dissolution profile is zero order, i.e., the rate of dissolution is independent of concentration.

A release profile, i.e., the extent of release of the magnesium over a desired time, can be conveniently determined for a given time by measuring the release under controlled conditions, e.g., using a USP dissolution apparatus. Preferred release profiles are those which slow the rate of uptake of the magnesium into the blood stream while providing therapeutically effective levels of the magnesium. According to standardized dissolution testing guidelines for controlled release ("CR") profiles, dissolution of the active ingredient is measured at given intervals over a period of time. A minimum of three time points is recommended and generally cover early, middle and late stages of the dissolution profile. The last measurement should be no earlier than the time point where at least 80% of the active ingredient is dissolved (Guidance for Industry, "Extended Release Oral Dosage Forms: Development, Evaluation, and Application of In Vitro/In Vivo Correlations", Food and Drug Administration, CDER, September 1997, Page 17). Adequate sampling is important: for example, at 1, 2 and 4 hours and every two hours thereafter until 80% of the active ingredient is released (Guidance for Industry, SUPAC-MR: Modified Release Solid Oral Dosage Forms," Food and Drug Administration, CDER, September 1997, Page 6). The preferred dissolution apparatus is USP apparatus I (basket) or II (paddle), used at recognized rotation speeds, e.g., 100 rpm for the basket and 50-75 rpm for the paddle (Guidance for Industry, "Extended Release Oral Dosage Forms: Development, Evaluation, and Application of In Vitro/In Vivo Correlations", Food and Drug Administration, CDER, September 1997, Page 4). Controlled release dosage forms permit the release of the active ingredient over an extended period of time. On the other hand, materials which dissolve at least 80% in the first 30 to 60 minutes in solution qualify as immediate release ("IR") profiles. ("Dissolution Testing of Immediate Release Solid Oral Dosage Forms", issued August 1997, Section IV-A). Therefore, immediate release solid oral dosage forms permit the release of most, or all, of the active ingredient over a short period of time, such as 60 minutes or less.

The subject composition may comprise an active ingredient including magnesium, threonate, or a threonate precursor. In one embodiment, the subject composition comprises a magnesium counter ion, as illustrated in the formula provided below:

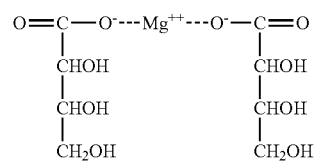

Such a composition may be prophylactically and/or therapeutically suitable or beneficial. Threonate is a natural metabolic product of vitamin C or ascorbic acid that may be associated with non-toxicity in animals (Thomas et al., *Food Chem.* 17, 79-83 (1985)) and biological benefit, such as the promotion of vitamin C uptake, in animals (Verlangieri et al., *Life Sci.* 48:2275-2281 (1991)).

In some embodiments, the threonate comprises threonate and/or threonate precursor molecules. Threonate can be in the form of a salt. The term "threonate precursor" generally means a precursor molecule that can be readily converted to threonate when the composition is dissolved in an aqueous media or ingested as a result of ionization or hydrolysis with or without the aid of an enzyme. The precursor can be a threonic acid, an ester derivative of threonic acid or threonate, or a lactonized threonic acid. Generally, threonate as used in the present invention refers to L-threonate. For example, an L-threonate precursor may be L-threonic acid, an ester derivative of L-threonic acid or L-threonate, or a lactonized L-threonic acid. In some embodiments, D-threonate or precursors thereof are used in the present invention.

In some embodiments, at least a portion of said magnesium (Mg) and threonate (T) is complexed in a salt form of $MgT_2$. In some embodiments, at least a portion of said magnesium (Mg) and threonate (T) is complexed in a salt form of $MgT_2$ present in an amount equal to at least about 20 mg of Mg by weight. In some embodiments, the molar ratio between said threonate (T) and said magnesium (Mg) is greater than or equal to about 0.1 to 2. In some embodiments, the magnesium (Mg) is present in an amount greater than about 1%, 2%, 3%, 4%, 5%, 6%, 7%, 8%, 9%, 10%, 11%, 12%, 13%, 14%, or 15% by weight. In some embodiments, the magnesium (Mg) is present in an amount greater than about 1%, 5%, or greater than about 7% by weight.

The compositions of the present invention generally comprise a sufficient amount (as defined further below) of magnesium ion (hereafter, "magnesium") and threonate or a threonate precursor molecule, wherein either magnesium or threonate may or may not be in the form of magnesium threonate in said compositions. When magnesium is not in the form of magnesium threonate but another magnesium salt, the other magnesium salt may be any suitable inorganic or organic magnesium salt. Herein, the term "suitable," generally means that the anion of the magnesium salt is nontoxic. Examples of suitable salts include, but are not limited to, magnesium salts of chloride, sulfate, oxide, acetate, lactate, citrate, malate, D-threonate, gluconate, taurinate, and pidolate. Similarly, when threonate is not in the form of magnesium threonate, it may be in the form of another threonate salt comprising another nontoxic cation. Suitable nontoxic cations include potassium, sodium, calcium and ammonium. In some embodiments, the suitable nontoxic cation is potassium. Generally, the present invention uses the term "threonate" to comprise threonate and precursors thereof, including salts, acids, esters and lactones, by way of example.

In addition to magnesium threonate, the compositions may comprise at least one magnesium-comprising component (MCC) or also used herein as magnesium-counter ion compound. Examples of an MCC include a magnesium salt of an amino acid, magnesium acetate, magnesium ascorbate, magnesium citrate, magnesium gluconate, magnesium lactate, magnesium malate, magnesium pyrrolidone carboxylate, and magnesium taurate. Alternate salts of the compositions disclosed herein include, but are not limited to, acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid. The term "salts" can also include addition salts of free acids or free bases. All of these salts (or other similar salts) may be prepared by conventional means. All such salts are acceptable provided that they are non-toxic and do not substantially interfere with the desired pharmacological activity.

An MCC composition of the present invention may comprise at least one component of non-acidified milk sufficient to enhance bioavailability of elemental magnesium associated with the MCC. Examples of such a component include lactose, a fatty acid or milk fat, and/or another organic component thereof, for example, sufficient for such enhancement. A mass ratio of the amount of elemental magnesium associated with the at least one MCC and the amount of the component may be from about 1 to about 5 to about 1 to about 3000. Such a composition may be suitable for oral administration to a subject.

Magnesium threonate is a highly bioavailable form of a magnesium counter-ion composition. However, the in vivo accessibility of this magnesium threonate may be provided in multiple ways. In some embodiments, a subject ingests magnesium threonate. In other embodiments, magnesium may be taken with other supplements which result in an in vivo reconstitution of magnesium-counter ion composition. Without being bound by theory, the threonate may function to promote cellular uptake of magnesium in any form and may also enhance delivery to the brain and central nervous system. Thus, in some embodiments, magnesium may be given uncomplexed with threonate and threonate is provided to the same subject to enhance absorption. For example, magnesium gluconate and potassium threonate may be taken near concurrently to result in an in vivo reconstitution of magnesium threonate and/or enhance magnesium uptake and/or delivery of magnesium to the brain. In another example, certain counter ions may be metabolic products of other substances. For example, vitamin C is metabolized into the threonate ion in humans; therefore, ingestion of magnesium in a form which can be taken up by the body and vitamin C may result in the reconstitution of magnesium threonate in the body. Another example of a substance which is metabolized to threonate in humans is ascorbate. Thus, in some embodiments of the present invention, magnesium ascorbate may be provided to a subject and this substance would be metabolized to magnesium and threonate in vivo. One of skill in the art will recognize that these examples are provided by way of illustration only and that other combinations of magnesium compounds and secondary compounds may result in the reconstitution of a magnesium-counter-ion composition in vivo.

A magnesium-counter ion composition comprising more than one magnesium-counter ion compound may be suitable, beneficial or desirable relative to a magnesium-counter ion composition comprising a single magnesium-counter ion compound. A combination of more than one magnesium-counter ion compound may be suitable, beneficial or desirable in terms of any number of features or factors, such as magnesium content, solubility, palatability, magnesium bioavailability, biological acceptability, and/or the like, for example. A combination of more than one magnesium-counter ion compound may be suitable, beneficial or desirable in terms of palatability. A combination of more than one magnesium-counter ion compound may be suitable, beneficial or desirable in terms of maintaining and/or enhancing an attribute or attributes of a magnesium-counter ion compound or several magnesium-counter ion compounds.

The relative amount of threonate-to-magnesium molar ratio can be adjusted for various formulations. Generally, the molar ratio of threonate-to-magnesium is >~1/5. Because each MgT contains 2 threonate, this means at least 10% of Mg is from MgT. The other 90% may be from $MgCl_2$ or other Mg salt. In some embodiments, the threonate-to-magnesium molar ratio is >~2/7. For example, this ratio corresponds to a nutraceutical formulation comprising about 50 mg Mg in the form of MgT and about 300 mg of Mg in the form of $MgCl_2$ or other Mg salt in a 350 mg Mg recommended daily allowance (RDA). In other embodiments, the threonate-to-magnesium molar ratio is about 2. In some embodiments, all threonate in said composition is in the form of magnesium threonate, which is the effective component of said compositions. When said magnesium and threonate are each part of separate compounds in the compositions and said compositions are dissolved or orally ingested, at least part of the magnesium and part of threonate will form magnesium threonate in situ as a result of ionic exchange reactions. In some embodiments, all of the magnesium and all of the threonate are from the same magnesium threonate compound, e.g., to minimize the mass of the composition. In some embodiments, when the threonate to magnesium molar ratio is less than 2, a portion of the magnesium comes from another magnesium compound. In some embodiments, the other magnesium compound is selected from magnesium chloride, magnesium taurinate, magnesium lactate, magnesium gluconate, magnesium citrate and magnesium malate.

The exact amount of magnesium used in a given dosage form of the present invention depends on the physical form of said composition. According to one embodiment, the invention provides a solid or semi-solid composition comprising at least 1%, 2%, 3%, 4%, 5%, 6%, 7%, 8%, 9%, or 10% or more elemental magnesium by weight. According to one embodiment, the solid or semi-solid composition is a pill comprising at least 20 mg elemental magnesium, or at least 50 mg of elemental magnesium, or at least 80 mg of elemental magnesium.

The controlled release compositions of the present invention have a number of advantages. For example, the invention can also enable a reduction in the dosing frequency. For example, the controlled release compositions of the present invention may be employed to administer the magnesium at a lower frequency than it would be with an immediate release formulation (i.e., once a day (q.d.) versus twice a day (b.i.d) or three times a day (t.i.d)), hence improving subject compliance and caregiver convenience. In some embodiments, the compositions described herein are administered even less frequently, e.g. every 2 days, every 3 days, every week, or every month. These compositions are particularly useful as they provide the magnesium at a biologically effective amount from the onset of administration further improving compliance and adherence and enable the achievement of an effective steady-state concentration of the magnesium in a shorter period of time. Furthermore, the compositions of the present invention, by virtue of their design, allow for higher doses of magnesium to be safely administered, again increasing the utility of these agents for a variety of indications.

Using the controlled release dosage forms provided by the present invention, the magnesium is released into a subject sample at a slower rate than observed for an immediate release (IR) formulation of the same quantity of magnesium. In some embodiments, the rate of change in the biological sample measured as the change in concentration over a defined time period from administration to maximum concentration for an controlled release formulation is less than about 80%, 70%, 60%, 50%, 40%, 30%, 20%, or 10% of the rate of the IR formulation. Furthermore, in some embodiments, the rate of change in concentration over time is less than about 80%, 70%, 60%, 50%, 40%, 30%, 20%, or 10% of the rate for the IR formulation. In some embodiments, the rate of change in concentration over time is less than about 5% of the rate for the IR formulation.

In some embodiments, the rate of change of concentration over time is reduced by increasing the time to maximum concentration in a relatively proportional manner. For example, a two-fold increase in the time to maximum concentration may reduce the rate of change in concentration by approximately a factor of 2. As a result, the magnesium may be provided so that it reaches its maximum concentration at a rate that is significantly reduced over an immediate release (IR) dosage form. The compositions of the present invention may be formulated to provide a shift in maximum concentration by 24 hours, 16 hours, 8 hours, 4 hours, 2 hours, or at least 1 hour. The associated reduction in rate of change in concentration may be by a factor of about 0.05, 0.10, 0.25, 0.5 or at least 0.8. In certain embodiments, this is accomplished by releasing less than about 30%, 50%, 75%, 90%, or 95% of the magnesium into the circulation within one hour of such administration.

Optionally, the controlled release formulations exhibit plasma concentration curves having initial (e.g., from 2 hours after administration to 4 hours after administration) slopes less than 75%, 50%, 40%, 30%, 20% or 10% of those for an IR formulation of the same dosage of the same magnesium. The precise slope for a given individual will vary according to the magnesium threonate composition, the quantity delivered, or other factors, including, for example, whether the patient has eaten or not. For other doses, e.g., those mentioned above, the slopes vary directly in relationship to dose.

Using the sustained release formulations or administration methods described herein, the magnesium reaches a therapeutically effective steady state plasma concentration in a subject within the course of the first 3, 5, 7, 9, 10, 12, 15, or 20 days of administration. For example, the formulations described herein, when administered at a substantially constant daily dose, e.g., at a dose ranging between 50 mg and 1000 mg, preferably between 100 mg and 800 mg, and more preferably between 200 mg and 700 mg per day of elemental Mg, may reach a steady state plasma concentration in approximately 70%, 60%, 50%, 40%, 30%, or less of the time required to reach such plasma concentration when using a dose escalating regimen.

In some embodiments, the rate of release of the magnesium from the present invention as measured in dissolution studies is less than about 80%, 70%, 60% 50%, 40%, 30%, 20%, or 10% of the rate for an IR formulation of the same magnesium over the first 1, 2, 4, 6, 8, 10, or 12 hours. In some embodiments, the rate of release of the magnesium from the present invention as measured in dissolution studies is less than about 80%, 70%, 60% 50%, 40%, 30%, 20%, or 10% of the rate for an IR formulation of the same magnesium over the first 2-4 hours. In some embodiments, the rate of release of the magnesium from the present invention as measured in dissolution studies is less than about 5% of the rate for an IR formulation of the same magnesium over the first 2-4 hours.

The controlled release dosage forms provided by the present invention can adopt a variety of formats. In some embodiments, the supplement composition of the present invention is administered in an oral dosage form, including liquid dosage forms (e.g., a suspension or slurry), and oral solid dosage forms (e.g., a tablet or bulk powder). In some embodiments, the dosage form is provided as a tablet. As used herein the term "tablet" refers generally to tablets, caplets, capsules, including soft gelatin capsules, and lozenges. The average tablet size for round tablets is preferably about 10 mg to 150 mg elemental Mg and for capsule-shaped tablets about 20 mg to 200 mg elemental Mg. Controlled release tablet generally fall into one of three categories: matrix, reservoir and osmotic systems. Although any of the three systems is suitable for the invention, the latter two systems have more optimal capacity for encapsulating a relatively large mass as may be desirable for the invention. In some embodiments, the slow-release tablet is based on a reservoir system, wherein the magnesium- and threonate-containing core is encapsulated by a porous membrane coating which, upon hydration, permits magnesium threonate to diffuse through. The effective daily dosage for human use can be about 50 to 1000 mg of magnesium, which corresponds to 606 to 12119 mg of magnesium threonate. The mass range will vary if magnesium and threonate are from compound sources other than magnesium threonate. Because the combined mass of the effective ingredients is generally in gram quantity, an efficient delivery system can provide optimal results.

Figure 6:
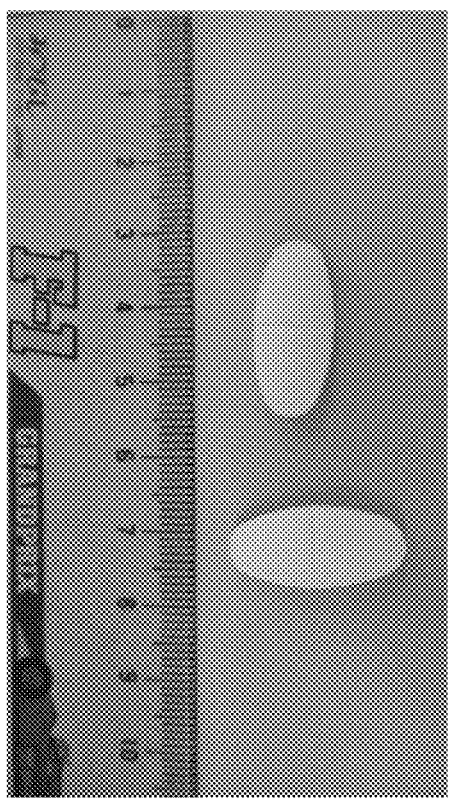
FIG. 6A illustrates a controlled-release tablet comprising magnesium threonate.
FIG. 6B illustrates the release profile of a controlled-release tablet comprising magnesium threonate formulated according to I.Example 6.
Figure 6:
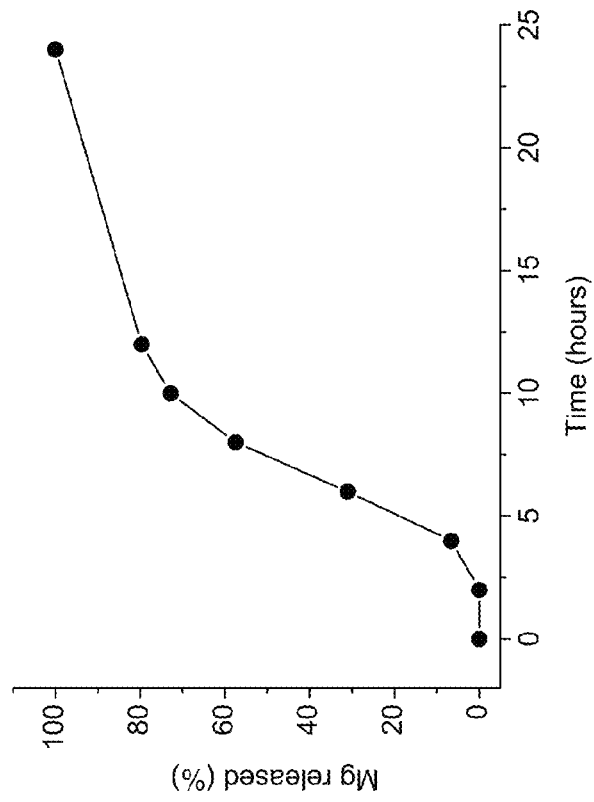

An example of controlled release tablet and its release profile are shown in FIG. 6, wherein the tablet comprises, in the core, magnesium threonate as magnesium composition, polyvinylpyrrolidone (PVP) as binder, magnesium stearate as lubricant and, in the coating, polyvinylacetate (SR30D) as matrix former, PVP as pore former, talc powder and $TiO_2$ as inert powders, propylene glycol as plasticizer and a lake dye. See I.Example 6 and Table 1. The tablet according to the above formulation exhibits a zero order release profile over a 24 hour period.

The present invention further provides methods of making oral dosage forms as disclosed herein. Tablets are made by methods known in the art and may further comprise suitable binders, lubricants, diluents, disintegrating agents, colorants, flavoring agents, flow-inducing agents, melting agents, many varieties of which are known in the art. The oral dosage forms of the present invention may, optionally, have a film coating to protect the components of the magnesium-counter ion supplement composition from one or more of moisture, oxygen and light or to mask any undesirable taste or appearance. Suitable coating agents include, for example, cellulose, hydroxypropylmethyl cellulose. In some embodiments, the oral dosage form comprises a plurality of beads encapsulated in a capsule. Such format can be used as a sustained release formulation. Other forms of tablets can also be formulated in sustained release format. Methods of making sustained release tablets are known in the art, e.g., see U.S. Patent Publications 2006/051416 and 2007/0065512, or other references disclosed herein.

In some embodiments, oral dosage form according to the present invention are made by mixing a powder comprising magnesium (Mg) and threonate (T), both of which can be present in a salt form, with a polymer in an amount sufficient to create particles comprising the magnesium (Mg), the threonate (T), and the polymer, wherein said particles are of a size sufficient to be retained by a 12 mesh sieve. In some embodiments, the method further comprising: filtering said particles to remove unbound threonate using the 12 mesh sieve; drying the particles; adding an acceptable amount of lubricant to said particles; compressing the particles into one or more pills of total size between about 100 mg and about 2000 mg and coating said one or more pills with a polymer coating comprising one or more of polyvinylpyrrolidone, polyvinyl acetate, and propylene glycol. In some embodiments, the pills are made with an elemental magnesium content of from about 10 mg to about 200 mg. In some embodiments, one or more forms of threonate contained within the dosage form comprises a threonate salt of a threonate precursor molecule as described herein. For example, a precursor may comprise threonic acid, a threonate ester, or a threonate lactone.

In some embodiments, the compositions described herein are prepared using formulations as described in U.S. Pat. No. 4,606,909, entitled "Pharmaceutical multiple-units formulation." This reference describes a controlled release multiple unit formulation in which a multiplicity of individually coated or microencapsulated units are made available upon disintegration of the formulation (e.g., pill or tablet) in the stomach of the subject (see, for example, column 3, line 26 through column 5, line 10 and column 6, line 29 through column 9, line 16). Each of these individually coated or microencapsulated units contains cross-sectionally substantially homogenous cores containing particles of a sparingly soluble active substance, the cores being coated with a coating that is substantially resistant to gastric conditions but which is erodable under the conditions prevailing in the gastrointestinal tract.

In some embodiments, the composition of the invention are formulated using the methods disclosed in U.S. Pat. No. 4,769,027, entitled "Delivery system," for example. Accordingly, extended release formulations of physiologically acceptable material (e.g., sugar/starch, salts, and waxes) may be coated with a water permeable polymeric matrix containing magnesium and next overcoated with a water-permeable film containing dispersed within it a water soluble particulate pore forming material.

In some embodiments, the magnesium composition is prepared as described in U.S. Pat. No. 4,897,268, entitled "Drug delivery system and method of making the same," for example, involving a biocompatible, biodegradable microcapsule delivery system. Thus, the magnesium may be formulated as a composition containing a blend of free-flowing spherical particles obtained by individually microencapsulating quantities of magnesium, for example, in different copolymer excipients which biodegrade at different rates, therefore releasing magnesium into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D, L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

In some embodiments, the composition of the present invention are prepared as described in U.S. Pat. No. 5,395, 626, which features a multilayered controlled release dosage form. The dosage form contains a plurality of coated particles wherein each has multiple layers about a core containing magnesium whereby the magnesium containing core and at least one other layer containing an active ingredient is overcoated with a controlled release barrier layer therefore providing at least two controlled releasing layers of a water soluble composition from the multilayered coated particle.

In some embodiments, the magnesium and threonate is prepared using the OROS® technology, described for example, in U.S. Pat. No. 6,919,373 entitled "Methods and devices for providing prolonged drug therapy;" U.S. Pat. No. 6,923,800, entitled "Osmotic delivery system, osmotic delivery system semipermeable body assembly, and method for controlling delivery rate of beneficial agents from osmotic delivery systems;" U.S. Pat. No. 6,929,803 entitled "Conversion of liquid filled gelatin capsules into controlled release systems by multiple coatings;" and U.S. Pat. No. 6,939,556 entitled "Minimally compliant, volume efficient piston for osmotic drug delivery systems;" all of which are hereby incorporated by reference. This technology employs osmosis to provide precise, controlled delivery for up to 24 hours and can be used with a range of compounds, including those that are poorly soluble. OROS® technology can be used to deliver high doses meeting high loading requirements. By targeting specific areas of the gastrointestinal tract, OROS® technology may provide more efficient absorption and enhanced bioavailability of the active ingredient. The osmotic driving force of OROS® and protection of the active ingredient until the time of release eliminate the variability of absorption and metabolism sometimes caused by gastric pH and motility.

Formulations for continuous long-term delivery are further provided in, e.g., U.S. Pat. No. 6,797,283, entitled "Gastric retention dosage form having multiple layers;" U.S. Pat. No. 6,764,697, entitled "System for delaying drug delivery up to seven hours;" and U.S. Pat. No. 6,635,268, entitled "Sustained delivery of an active agent using an implantable system;" all of which are incorporated herein by reference.

In some embodiments, the controlled release dosage forms of the present invention comprise a plurality of beads, wherein each bead includes a core having a diameter from about 1 μm to about 1000 μm and the core includes an active ingredient comprising magnesium or a salt thereof in the range of about 15 to about 350 mg Mg/g of the dosage form, wherein the dosage forms include less than about 2.5% adduct and has a dissolution rate of the active ingredient of more than about 80% within about the first 60 minutes following entry of the dosage forms into a use environment. In some embodiments, the dissolution rate is more than about 80% within 30 minutes.

In some embodiments, each bead includes a core and an active ingredient comprising magnesium. A suitable bead form of magnesium may comprise magnesium and threonate admixed with soluble components, e.g., sugars (e.g., sucrose, mannitol, etc.), polymers (e.g., polyethylene glycol, hydroxypropyl cellulose, hydroxypropyl methyl cellulose, etc.), surfactants (sodium lauryl sulphate, chremophor, tweens, spans, pluronics, and the like), insoluble glidant components (microcrystalline cellulose, calcium phosphate, talc, fumed silica, and the like), coating material (examples of suitable coating materials are polyethylene glycol, hydroxypropyl methyl cellulose, wax, fatty acids, etc.), dispersions in suitable material (examples are wax, polymers, physiologically acceptable oils, soluble agents, etc.) or combinations of the above.

According to some embodiments, the core includes sugar spheres (nonpareil seeds), microcrystalline cellulose, or mannitol. In some embodiments, the core is a sugar sphere, USP (Paulaur Cranbury, N.J.). In some embodiments, the particle size of the core ranges from about 1 μm to about 1000 μm. In some embodiment, the particle size of the core ranges from about 300 μm to about 900 μm. In some embodiment, the particle size of the core ranges from about 450 μm to about 825 μm. In exemplary embodiments, the core may be coated to avoid interaction between the core and the active ingredient. For example, suitable coating materials include, but are not limited to, polyethylene glycol, hydroxypropyl methyl cellulose, wax, fatty acids, etc.

In one embodiment, the spheres comprise a portion of the dosage form ranging from about 50 mg/g to about 500 mg/g, preferably from about 60 mg elemental magnesium per g of oral dosage form (i.e., 60 mg Mg/g), to about 100 mg elemental magnesium per g of oral dosage form (i.e., 100 mg Mg/g). The fraction of the bead will depend on the amount of additional constituents, if any, used in the dosage form.

The core can be coated with magnesium, e.g., magnesium threonate. In one embodiment, magnesium threonate is present in amounts from about 150 mg/g (or 12.4 mg Mg/g) to about 950 mg/g (or 78.4 mg Mg/g), preferably from about 500 to 900 mg/g (or 41.2 to 74.3 mg Mg/g) based on the weight of the entire IR bead. In other embodiments, magnesium is present in amounts from about 15 to 300 mg/g, preferably from about 25 to about 250 mg/g.

In one embodiment, magnesium threonate is added to a mixture of a binder and a glidant prior to coating the core. The glidant may be selected from, but is not limited to, microcrystalline cellulose, calcium phosphate, talc, and fumed silica. Glidants may be used in amounts ranging from 1.5 mg/g to about 35 mg/g. In some embodiments, glidants range from about 1.5 mg/g to about 30 mg/g. In some embodiments, glidants range from about 2.5 mg/g to about 25 mg/g. In another embodiment, the range of glidant is from about 5 mg/g to about 30 mg/g.

The binder may be selected from, but is not limited to, povidone (PVP), hydroxypropyl methylcellulose (HPMC, Opadry), hydroxypropyl cellulose (HPC), or combinations thereof. In an embodiment where the binder is HPMC, the binder is present in an amount ranging from about 15 mg/g to about 30 mg/g, preferably from about 15 mg/g to about 25 mg/g. In another embodiment, where the binder is povidone, the binder is present in an amount of from about 1.5 mg/g to about 35 mg/g, preferably from about 5 mg/g to about 30 mg/g.

The mixture of active ingredient and binder/water/glidant may be prepared by mixing, e.g., with a stirrer, for at least 15 minutes, for at least 30 minutes, or for at least one hour. The components may also be combined by methods including blending, mixing, dissolution and evaporation, or by using suspensions.

The active ingredient/binder/inactives mixture may be deposited on a core, wet massed and extruded, granulated, or spray dried. In one embodiment, sugar spheres are pre-warmed to a temperature ranging from about 40° C. to about 55° C. prior to application of the mixture. The core may be optionally coated with from about 2% w/w to about 10% w/w seal coating prior to applying the active layer. The seal coating may be any applicable coating which can separate any active ingredients from the core, for example, polymer coatings such as Eudragit®, HPMC, HPC, or combinations thereof. For this reason also, dissolution stability (i.e., maintenance of dissolution profile after exposure to elevated temperatures) is important for the compositions of the present invention.

In one embodiment, the sugar sphere are coated with a fluidized bed coater known in the art, for example, a Glatt Powder Coater and Granulator, GPCG3 (Ramsey, N.Y.). One skilled in coating conditions such as air velocity, spray rate, and atomization pressure are typically controlled as is appreciated by and known to those skilled in the art. The temperature range of the product may range from about 43° C. to about 51° C. The air velocity may range from about 5 to about 9 m/s. The spray rate ranges from about 9 to about 42 gm/min. The atomization pressure can range from about 1.5 to about 2.0 bar. The beads are then dried in the fluidized bed of the coating apparatus at a temperature of about 45° C. to about 50° C. for at least 5 minutes. In some embodiments, the beads are dried for at least 15 minutes, or for at least 30 minutes. One skilled in the art will recognize that many alternate operating conditions and various types of equipment can also be used.

Once the IR beads are formed as cores containing magnesium threonate as provided herein, the beads may be optionally additionally coated with a seal coating. The seal coating may be a polymer or a combination of polymers that can be designed to be pH dependent or independent. In a preferred embodiment, the polymer for the seal coating is selected from, but are not limited to HPMC (Opadry®, Colorcon, PA), HPC, Eudragit® RL, Eudragit® E100, Eudragit® E 12.5, Eudragit®, E PO, Eudragit® NE (e.g., NE 30D or NE 40D) and combinations of two or more of the foregoing. These polymers are insoluble in aqueous media but display pH-independent swelling on contact with aqueous fluids. In another embodiment, the IR beads are coated with pH-dependent polymers, soluble at a pH preferably above 5. In the IR bead formulations, the seal coating polymer is present in amounts ranging from about 0% w/w to about 40% w/w, preferably from about 0% w/w to about 10% w/w, more preferably from about 0% w/w to about 3% w/w.

Alternatively the IR cores may be coated with a rapidly disintegrating or dissolving coat for aesthetic, handling, or stability purposes. Suitable materials are polyvinylpyrrolidone, hydroxypropyl cellulose, hydroxypropyl methyl cellulose, polyethylene glycol, polymethacrylates containing free amino groups, each may be with or without plasticizers, and with or without an antitack agent or filler. An addition of about 3% of the weight of the core as coating material is generally regarded as providing a continuous coat for this size range. The over coating may be a polymer selected from, but are not limited to HPMC (Opadry®, Colorcon, PA), HPC, Eudragit® RL, Eudragit® E100, Eudragit® E 12.5, Eudragit® E PO, Eudragit® NE and mixtures thereof.

Dissolution of the active agent, e.g., magnesium threonate, from the beads can occur by the penetration of the bulk medium and diffusion across the polymer layer, which are in turn controlled by the permeability and swelling properties of the polymer. In some embodiments, the modified release beads have near bioequivalent AUC (area under the curve, a measure of bioavailability) as compared to an immediate release tablet dosage form, and a reduced maximum plasma concentration of at least 25% relative to the immediate release tablet. The modified release bead demonstrates good tolerability and can be administered over a wide range of dosages. In some embodiments, the maximum plasma concentration is less than about 85% of the immediate release tablets when administered as a single dose. In some embodiments, the AUC is within 75% to 130% of the immediate release tablets administered as a single dose. This range is considered equivalent with respect to overall systemic exposure.

All of the beads from the controlled release formulation need not release immediately. This can prevent dose dumping and to reduce adverse events. In some embodiments, the average time to reach maximum plasma concentration ranges from between about 5 to about 48 hours, or from about 5 to about 36 hours. In some embodiments, the beads have an in vitro release rate of more than about 70% to about 80% in about 4 to about 12 hours. In some embodiments, the formulations have a release rate of about 30% to about 60% in about 2 to about 6 hours. In some embodiments, the formulations have a release rate of about 10% to about 50%, or about 10% to 35% within the first hour following entry into a use environment followed by extended release.

In other embodiments, the present invention provides a composite dosage form comprising an immediate release (IR) component and a controlled release (CR) component, wherein the immediate release component comprises a first plurality of beads, each bead comprising a first active ingredient comprising magnesium or a salt thereof in the range of about 15 to about 350 mg/g of the dosage form, wherein about 80% of the first active ingredient dissolves within about the first 60 minutes following entry of the dosage form into a use environment; and wherein the modified release component comprises a second plurality of beads, each bead comprising a second active ingredient comprising magnesium or a salt thereof in the range of about 15 to about 350 mg/g of the dosage form, wherein about 70% to about 80% of the second active ingredient dissolves within about 4 hours to about 24 hours following entry of the dosage form into the use environment.

The composite dosage form may be combined into a single dosage form having a uni-phase or multi-phase profile. The active ingredient, e.g., magnesium threonate, in the composition may be present in amounts measured as mg per dose, ranging from about 2.5 mg to about 100 mg per dose. Preferably, the doses contain 2.5 mg to 80 mg active ingredient. In other embodiments, the dose is 3, 6, 7, 9, 12, 14, 15, 20, 21, 28, 40 or 60 mg.

The compositions including an IR and CR component may include an amount of magnesium in the immediate release form of approximately 5% to 90% of the composition of the invention. In some embodiments, the immediate release portion is about 10% to 60%. In some embodiments, the immediate release magnesium content ranges from about 15% to 50%. The controlled release form of the magnesium may constitute the remainder of the active ingredient. As a result, a final composition provides an amount of magnesium for immediate release following administration and an additional amount for sustained/modified release. The composition of the invention may exhibit more than one peak in the plasma concentration/time curve in any one dosing interval depending on a particular active ingredient used, relative amounts of the IR and CR components, and the dissolution properties of the CR component. Thus, compositions may be achieved that have specific release profiles.

The compositions including an IR and CR component may include any solid oral dosage forms known in the art. E.g., solid dosage forms used in the present invention include beads. Beads are dose proportional, i.e., the same proportions of beads of different types can be used for different doses without significantly altering the percentage of active ingredient released over time. For example, a 40 mg dose will deliver twice the magnesium as a 20 mg dose, with proportional bioavailability. Different doses are obtained by using different amounts of beads. Beads also enable a variety of dissolution profiles by mixing one or more types of beads with different dissolution properties or using multi-layer coatings, as additional layering of active ingredients over a polymer layer and subsequent coatings to prepare unitary beads, as familiar to one skilled in the art. Beads also enable a wide range of loading. For example, magnesium beads may be loaded on beads at up to 500 mg/g dosage form, depending on the form of magnesium, counter ions, and the like. One skilled in the art will recognize that higher loading allows for smaller capsule size.

Prolonging the time to maximum plasma concentration as compared to immediate release tablet, is related to the release rate of the magnesium in the use environment. The release rate of the magnesium depends on many factors, including the composition of the solid dosage forms and the dissolution properties. By using different compositions containing either unitary beads or a combination of a plurality of bead types, their individual release rates can be combined to achieve desired plasma release profiles. Beads with different release characteristics can be achieved by selection of the release-modifying polymer, as well as the combination of the release-modifying polymer and the binder to impart different release characteristics to the resulting beds. Overcoats such as enteric coatings can also be used, if desired.

The beads or bead mixtures may be used, for example, in suspensions, filled into capsules, compressed into tablets, or filled into sachets. One or more types of modified release beads can be mixed together and encapsulated, or used as a sprinkle on the subject's food. According to the invention, the oral solid dosage form may be any of these forms. Preferably, the dosage form is a capsule.

In one embodiment of the invention, the beads are formulated into capsules with the use of an encapsulation machine. Various capsule sizes may be required to accommodate the strength and fill weight of the target formulations. Capsule size range from 00 to 5 for fill weights ranging from about 15 mg to about 630 mg.

The particle sizes of the IR and CR bead components in the dosage form depend on the technology used to prepare them. The particle sizes component range from submicron to 500 µm for powder technologies (mixtures, spray drying, dispersions etc), 5 to 1700 µm for coating technologies (Wurster®, top spray, bottom spray, spray drying, extrusion, layering, etc.), to 1-40 mm for tabletting technologies.

In addition to the active ingredients comprising magnesium and threonate, the oral dosage forms of the present invention can comprise any numbers of physiologically acceptable excipients, depending in part on the controlled release mechanism to be used. "Physiologically Acceptable" includes molecular entities and compositions that do not produce an adverse, allergic or other untoward reaction when administered to an animal, or a human, as appropriate, e.g., those that are pharmaceutically acceptable. "Physiologically Acceptable Carrier" includes any and all solvents, dispersion media, coatings, antibacterial and antifungal agents, isotonic and absorption delaying agents and the like. The use of such media and agents for physiologically active substances is well known in the art. Except insofar as any conventional media or agent is incompatible with the active ingredient, its use in the magnesium threonate compositions is contemplated. Supplementary active ingredients can also be incorporated into the compositions. "Physiologically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations.

By way of example, extended or modified release oral formulation can be prepared using additional methods known in the art. For example, a suitable extended release form of the magnesium threonate compositions provided herein may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are useful when the active ingredients, e.g., different forms of magnesium and threonate, have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The compositions of the present invention comprise one or any combinations of excipients such as, but not limited to, diluents, binders, disintegrants, glidants, lubricants, colorants, flavouring agents, solvents, film forming polymers, plasticizers, opacifiers, antiadhesives, and polishing agents. The compositions of the present invention may be formulated using any of the following excipients or combinations thereof.

TABLE 1

| Excipient name | Chemical name | Exemplary Function |
| --- | --- | --- |
| Avicel PH102 | Microcrystalline Cellulose | Filler, binder, wicking, disintegrant |
| Avicel PH101 | Microcrystalline Cellulose | Filler, binder, disintegrant |
| Eudragit RS-30D | Polymethacrylate Poly (ethyl acrylate, nethyl methacrylate, timethylammonioethyl methacrylate chloride) 1:2:0.1 | Film former, tablet binder, tablet diluent; Rate controlling polymer for controlled release |
| Methocel K100M Premium CR | Hydroxypropyl methylcellulose | Rate controlling polymer for controlled release; binder; viscosity-increasing agent |
| Methocel K100M | Hydroxypropyl methylcellulose | Rate controlling polymer for controlled release; binder; viscosity-increasing agent |
| Magnesium Stearate | Magnesium Stearate | Lubricant |
| Talc | Talc | Dissolution control; anti-adherent, glidant |
| Triethyl Citrate | Triethyl Citrate | Plasticizer |
| Methocel E5 | Hydroxypropyl methylcellulose | Film-former |
| Opadry ® | Hydroxypropyl methylcellulose | One-step customized coating system which combines polymer, plasticizer and, if desired, pigment in a dry concentrate. |
| Surelease ® | Aqueous Ethylcellulose Dispersion | Film-forming polymer; plasticizer and stabilizers. Rate controlling polymer coating. |

The magnesium compositions described herein may also include a carrier such as a solvent, dispersion media, coatings, antibacterial and antifungal agents, isotonic and absorption delaying agents. The use of such media and agents for pharmaceutically active substances is well known in the art. Acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, entitled "Heterovesicular liposomes," PCT applications WO 95/13796, entitled "Vesicles with Controlled Release of Actives," or WO 91/14445, entitled "Heterovesicular Liposomes," or European patent EP 524,968 B1, may also be used as a carrier.

The oral dosage forms of the present invention can comprise a variety of excipients. Surfactants which may be used in the present invention as a compressibility augmenting agent generally include all physiologically acceptable, e.g., pharmaceutically-acceptable, surfactants. Suitable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the formulation arts, sodium lauryl sulfate has been used as an emulsifying agent in amounts of up to about 0.1% by weight of the formulation. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone.

Other suitable surfactants include acacia, benzalkonium chloride, cholesterol, emulsifying wax, glycerol monostearate, lanolin alcohols, lecithin, poloxamer, polyoxyethylene, and castor oil derivatives. Those skilled in the art will further appreciate that the name and/or method of preparation of the surfactant utilized in the present invention is not determinative of the usefulness of the product.

Highly polar molecules may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is physiologically (e.g., pharmaceutically) acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfonic acid]disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo) naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hydroxy-6-[7-sulfonato-4-(4-sulfonatophenylazo)-1-naphthylazo] naphthalene-1,7-disulfonate); Carmoisine (chemical name: Disodium 4-hydroxy-3-(4-sulfanato-1-naphythylazo) Naphthalene-1-sulfonate); Amaranth (chemical name: Trisodium 2-hydroxy-1-(4-sulfonato-1-naphthylazo) naphthalene-3,6-disulfonate); and mixtures thereof.

Other highly polar molecules which may be utilized as the compressibility augmenting agent include optional additional active agents themselves. For example, it is well-known to those skilled in the art that certain classes of pharmaceuticals, such as anti-psychotic drugs, are highly polar in nature and may be utilized as a compressibility augmenting agent in accordance with this invention.

The usable concentration range for the selected surfactant depends in part upon not only its molecular weight but also its degree of foaming, particularly when present in agitated slurries which will be spray dried to form the desired particulate. Thus, in those aspects of the invention where surfactants other than sodium lauryl sulfate are coprocessed with the magnesium threonate, it is to be understood that the surfactant will be present in an amount which enhances the compressibility of the magnesium threonate and yet does not have a degree of foaming which would substantially inhibit spray drying.

In an embodiment utilizing a spray-drying process, an aqueous dispersion of magnesium threonate and a compressibility augmenting agent (for example, a surfactant or silicon dioxide) is brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles may be approximately spherical in shape and may be relatively uniform in size, thereby possessing excellent flowability. The coprocessed particles are not necessarily uniform or homogeneous. Other drying techniques such as flash drying, ring drying, micron drying, tray drying, vacuum drying, radio-frequency drying, and possibly microwave drying, may also be used.

Alternatively, all or part of the excipient may be subjected to a wet granulation with an active ingredient. A representative wet granulation includes loading the novel excipient particles into a suitable granulator, such as those available from Baker-Perkins, and granulating the particles together with the active ingredient, preferably using an aqueous granulating liquid. In some embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with other excipients commonly used by those skilled in the art, depending of course upon the requirements of the particular formulation.

In other embodiments of the invention, a further material is added to the magnesium threonate and/or compressibility augmenting agent. Such additional materials include silicon dioxides, non-silicon metal oxides, starches, starch derivatives, surfactants, polyalkylene oxides, cellulose A ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional additives known to those skilled in the art can be added to the novel excipient prior to preparation of the final product. For example, if desired, any generally accepted soluble or insoluble inert filler (diluent) material can be included in the final product (e.g., a solid dosage form). Such inert fillers may comprise a monosaccharide, a disaccharide, a polyhydric alcohol, inorganic phosphates, sulfates or carbonates, and/or mixtures thereof. Examples of suitable inert fillers include sucrose, dextrose, lactose, xylitol, fructose, sorbitol, calcium phosphate, calcium sulfate, calcium carbonate, microcrystalline cellulose, mixtures thereof, and the like.

An effective amount of any generally accepted lubricant, including calcium or magnesium soaps may optionally be added to the excipient at the time the magnesium is added, or in any event prior to compression into a solid dosage form. The lubricant may comprise, for example, magnesium stearate in any amount of about 0.5-3% by weight of the solid dosage form. In embodiments where a surfactant is included as part or all of the compressibility augmenting agent, an additional inclusion lubricant may not be necessary.

The complete mixture, in an amount sufficient to make a uniform batch of tablets, may then subjected to tableting in a conventional production scale tableting machine at normal compression pressures for that machine, e.g., about 1500-10,000 lbs/sq in. The mixture should not be compressed to such a degree that there is subsequent difficulty in its hydration when exposed to gastric fluid.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

In some embodiments, the magnesium (Mg) is complexed with an anion selected from the group consisting of chloride, taurinate, lactate, gluconate, citrate, malate, succinate, sulfate, propionate, hydroxide, oxide, orotate, phosphate, borate, salicylate, carbonate, bromide, stearate, an amino acid, butyrate, aspartate, ascorbate, picolinate, pantothenate, nicotinate, benzoate, phytate, caseinate, palmitate, pyruvate, and threonate. In some embodiments, the oral dosage forms comprise a metal ion selected from the group consisting of calcium, potassium, sodium, chromium, iron, selenium, zinc, manganese, molybdenum, vanadium, and lithium. In some embodiments, one or more antioxidants are added to the composition, e.g., resveratrol, ellagic acid, quercetin, lipoic acid or vitamin C.

In addition to the excipients listed above, the oral dosage forms of the present invention contain one or more chemicals or one or more extracts obtained from the nature. Listed below are examples of nutritional ingredients and health ingredients that can be provided according to the present invention.

Examples of nutritional ingredients with which magnesium threonate can be mixed include 5-HTP (5-hydroxytryptophan), 7-keto-DHEA (dehydroepiandrosterone), acetate, acetyl-L-carnitine, AE-941, α-carotene, α-hydroxy acids, α-aminohydrocinnamic acid, α-ketoglutarate, α-galactosidase, α-linolenic acid, α-lipoic acid, α-tocopherol, SHA-10, androstenediol, androstenedione, arginine, aspartic acid (aspartate), ascorbic acid, β-alanine, β-alanyl-L-histidine, β-carotene, β-cryptoxanthin, β-D-fructofuranosidase, betadine, β-glucan, β-glycans, betaine, β-sitosterol, β-tocopherol, BMS-214778, calcium carbonate matrix, calcium phosphate, caprylic acid, canthaxanthin, CDP-choline, chelated calcium, cholecalciferol, choline, chondroitin sulfate, citicoline, citric acid, creatine, cryptoxanthin, cysteine, D-calcium pantothenate, dehydroepiandrosterone, delta-tocopherol, dexpanthenol, dextran-iron, DGL (deglycyrrhiziated licorice), EA (Dehydroepiandrosterone), dibencozide, dichloroacetate, dimethylglycine, dimethylsulfone, disodium disuccinate astaxanthin, D,L-phenylalanine, DMAE (Dimethylaminoethanol), D-mannose, DMSO (dimethyl sulfoxide), docosahexaenoic acid, docusate sodium, eburnamenine-14-carboxylic acid, EDTA (ethylenediamine tetraacetic acid), EFA (essential fatty acid), ellagic acid, eicosapentaenoic acid, ferrous gluconate, ferrous sulfate, 5-hydroxytryptophan, flavonoid, folacin, folate, folic acid, forskolin, fructo-oligosaccharides, GABA (gamma-aminobutyric acid), galanthamine hydrobromide, γ-carotene, γ-linolenic acid, γ-oryzanol, γ-glutamylcysteinylglycine, γ-tocopherol, glucosamine, glucosamine sulfate, glutamine, glutamic acid, glutathione, glycerol, glycerophosphocholine, glycine, histidine, HMB (β-hydroxy-β-methylbutyrate monohydrate), hydroxocobalamin, hydroxycitric acid, hydroxymethylbutyrate, hydroxytryptophan, hyoscine butylbromide (scopolamine), hydroxylysine, hydroxyproline, hypoxanthine riboside, indole-3-carbinol, inosine, inositol hexanicotinate, inositol hexaphosphate, isoascorbic acid, isoflavones, isoleucine, lactic acid, L-arginine, L-ascorbic acid, L-asparagine, L-carnitine, L-Dopa, leucine, L-phenylalanine, L-tryptophan, luzindole, lycopene, lysine, malic acid, mesoglycan, methionine, methylcobalamin, methylguanidine acetic acid, methylsulfonylmethane, monounsaturated fatty acid, N-3 fatty acids, N-acetyl cysteine, N-acetyl D-glucosamine, N-acetyl-5-methoxytryptamine, N-acetylaspartic acid, NADH, niacin, nicotinamide adenine dinucleotide, nordihydroguaiaretic acid (NDGA), octacosanol, octanoic acid, oleuropein, omega-3 fatty acids, omega-6 fatty acids, omega-9 fatty acid, PABA (para-aminobenzoic acid), pangamic acid, pantethine, pantothenic acid, pantothenol, perillyl alcohol, PGGi-glucan, phenylacetate, phosphatidylcholine, phosphatidylserine, phytoestrogen, phytonadione, phytosterols, polyphenols, polysaccharide-K, polyunsaturated fatty acids, polyvinylpyrrolidone-iodine, potassium, potassium aspartate, potassium phosphate, povidone-iodine, pregnenolone, progesterone, provitamin a, pteroylglutamic acid, pyridoxine, pyridoxal-5-phosphate, quercetin, quercetin-3-rhamnoglucoside, quercetin-3-rutinoside, quinine, resveratrol, retinol, riboflavin, riboflavin-5-phosphate, salicin, salicylate, SAM-e (S-adenosylmethionine), sitostanol, sitosterol, sitosterolins, sodium alginate, sodium ascorbate, sodium chloride, sodium ferric gluconate, sodium iodide, sodium phenylacetate, sodium phosphate, sorbic acid, stigmasterol, sulforaphane, synephrine, tannic acid, theanine, theobromine, thiamin, thioctic acid, tocopherols, tocotrienols, triacylglycerol lipase, tricholine citrate (TRI), troxerutin, tryptophan, tyrosine, acetyl-L-tyrosine, ubidecarenone, ubiquinone, urosolic acid, usnic acid, valine, vitamin A, vitamin B1, vitamin B12, vitamin B2, vitamin B3, vitamin B5, vitamin B6, vitamin B9, vitamin Bx, vitamin C, vitamin D, vitamin D2, vitamin D3, vitamin E, vitamin G, vitamin H, vitamin K, vitamin M, vitamin 0, vitamin Q10, xylitol, or zeaxanthin.

Examples of nutritional ingredients which are herbal or natural extracts with which magnesium threonate can be incorporated include aaron's rod (verbascum thapsus), abelmoschus moschatus, abrus precatorius, absinthe, abuta, acacia, acacia senegal, acai, acemannan, acerola, achicoria, achillea millefolium, achiote, ackee, aconite, aconitum napellus, acorus calamus L., actaea racemosa L., *actinidia chinensis, actinidia deliciosa*, adam's needle, adelfa, adrue, aegle marmelos, *aesculus hippocastanum* L., african wild potato, agathosma betulina, agave americana, agave sisalana, agrimonia eupatoria, agrimonia odorata, agrimonia procera, agrimony, *agropyron repens*, aguacate, alanine, albahaca morada, albaricoque, albarraz, alchemilla vulgaris, alcusa, alder, alfalfa, algarrobo, algin, alizarin, alkanet tinctoria, *allium cepa, allium sativum, allium ursinum*, allspice, almendra amarga, almendra dulce, aloe, aloe barbadensis, aloe ferox, aloe vera, alpine cranberry, alpinia galanga, alpinia officinarum, althaea officinalis, aluminum phosphate, amanita muscaria, amaranth, amargo, ambrette (abelmoschus moschatus), american aloe, american hellebore, american pawpaw, american pennyroyal, american scullcap, american valerian, american white water lily, american yew, aminobenzoic acid, amla fruit, ammi visnaga, amomum, *anacardium occidentale, ananas comosus, ananas sativus*, anapsos, anchusa, andiroba, andrographis paniculata, anemone acutiloba, angelica sinensis, angel's trumpet, angostura trifoliata, anis estrellado, annatto, annona muricata, annual mugwort, annual wormwood, antelaea azadirachta, anthemis grandiflorum, anthemis nobilis, anthozoa, antineoplastones, antineoplastons, AFA (aphanizomenon flos-aquae), *apis cerana, apis mellifera*, apium graveolens, apocynum cannabinum, apple cider vinegar, apricot, *arachis hypogaea*, arbre fricassee, arbutin, arcilla, arctium lappa, arctium majus, arctostaphylos, arctostaphylos uva-ursi, *areca catechu* L., arecoline, aristolochia, armeniaca vulgaris, armoracia rusticana, arnica montana, arrowroot, arsenicum album, *artemisia absinthium, artemisia annua, artemisia vulgaris*, arthrospira plantensis, artichoke, artocarpus heterophyllus, arundinaria japonica, asafoetida, asarabacca, asarum, asclepias tuberosa, *ascophyllum* nodosum, ashwagandha, asian ginseng, asimina americana, asimina triloba, asophyllum nodosum, aspalathus linearis, asparagus, *asparagus officinalis*, aspen, asperula odorata, aspérula olorosa, astaxanthin, astaxantina, asthma weed, astrágalo, *astragalus, astragalus* membranaceus, atropa belladonna, australian tea tree oil, autumn crocus, aveloz, *avena* extract, avocado, azadirachta indica, ba ji tian, babassu, baccharis genistelloides, baccharis trimera, baccharis triptera, bacopa, bacopa monnieri, bael fruit, baikal skullcap, ballota nigra, balm of gilead, balsam herb, bamboo, bantu tulip, banxia houpo tang, baptisia australis, barbados cherry, barberry, bardana, barosma betulina, bay leaf, bayberry, bear's garlic, bearberry, bedstraw, bee pollen, beeswax, beet, bejunco de cerca, belcho (ephedra sinica), belladona, bellis perennis, bentonite, berberina, berberine, berberis aristata, berberis vulgaris, bergamot oil, β-vulgaris, betel nut, betony, *betula* spp., bifidobacteria, bilberry, biminne, bing gan tang, birch sugar, birthwort, bishop's weed, bismuth, bitter almond, bitter aloe, bitter ash, bitter gourd, bitter melon, bitter orange, bitter wood, bitterroot, bixa orellana, biznaga, black bryony, black cohosh, black currant, black haw, black horehound, black mulberry, black mufstard oil, black pepper, black seed, black tea, blackberry, black cherry, black walnut, bladderwrack, blessed thistle, blighia sapida, bloodroot, blue cohosh, blue flag root, blue rocket (aconite), blueberry, blue-green algae, bluperum, boldo, boneset, borage seed oil, borago officinalis, borforsin, *boswelia carterii*, boswellia sacra, boswellia serrata, bovine cartilage, boxwood, brahmi, *brassica* campestris oil, *brassica nigra, brassica oleracea*, brazilian vetiver, bromelain, broom corn, brugmansia, bryonia, b-sitosterol, buchu, buckhorn plantain, buckshorn plantain, buckthorn, buckwheat, bugleweed, bulbous buttercup, bupleurum, burdock, butanediol, butcher's broom, butterbur, buxus sempervirens L., cabbage rose, cactus prickly pear, cajeput oil, calaguala, calamus, calcitriol, *calendula*, california jimson weed, california poppy, calophyllum inophyllum L., calostro bovino, *camellia sinensis*, campesterol, camphor, canadian hemp, cancer weed, *cannabis* sativa, canola oil, cantharis, *capsella* bursa-pastoris, *capsicum, carapa* ssp., caraway, caraway oil, carbohydrate supplement, cardamom, cardamomo, cardo bendito, cardo lechero, *carica papaya*, carnitine, carnosine, carob, carotene, carqueja (baccharis genistelloides), carrageenan, carrot, *carthamus tinctorius*, cascara sagrada, cashew, castaña de indias, castor oil, castor seed, caterpillar fungus, catha edulis, catnip, cat's claw, cat's hair, catuaba, caulophyllum thalictroides, cayenne, cebada, cebolla albarrana, cedar leaf oil, celandine, cemphire, centaurea benedicta, centaurea cyanus, centella asiatica, century plant (agave americanan), cephaelis ipecacuanha, ceratonia asiatica, ceratonia siliqua, cervus elaphus, cervus nippon, cetyl myristoleate, ceylon citronella, chamaemelum nobile, chamomile, chaparral, chasteberry, chaste tree, chelidonium majus, *chenopodium quina, chenopodium* vulvaria, chewing tobacco, chia, chickweed, chicory, chili pepper, china rose, chinese angelica, chinese boxthorn, chinese foxglove, chinese gelatin, chinese ginger, chinese ginseng, chinese matrimony vine, chinese star anise, chinese wormwood, chintul, chirayata, chitosan, *chlorella*, Cholestin®, chrysanthemum, chrysanthemum vulgare, chrysin, chrysopogon spp., cichorium intybus, cicuta virosa, cider vinegar, *cimicifuga racemosa, cinnamomum* aromaticum, cinnamon, cissampelos pareira, citrillus colocynthis, citronella grass, citrulline, citrus aurantifolia, citrus aurantium, citrus bergamia, citrus naringinine, citrus paradisi, citrus reticulata, *claviceps purpurea*, clavo de olor, cloud mushroom, clove, club moss, cnidium monnieri, cobalamin, coca, coccinia indica, cochlearia armoracia, cockleburr, coconut oil, codonopsis, coenzyme Q10, coenzyme R, cohosh azul, cohosh negro, cola nut, colchicum, coleus forskohlii, coltsfoot, colubrina arborescens, comfrey, commifora mukul, *commiphora molmol, commiphora myrrha*, condurango, cone flower, conium maculatum, consuelda, copaiba balsam, copaifera officinalis, coptis formula, coral calcium, cordyceps sinensis, *coriolus mushroom, coriolus versicolor*, corn poppy, corn silk, corn sugar gum, cornflower, cornus spp., corydalis, corylus avellana, corynanthe yohimbi, costmary, cottonseed oil, cottonwood, couch grass, cow parsnip, cowbane, cowhage, cowslip (primula veris), crab's eye, cramp bark, cranberry, cranesbill, *crataegus*, cumin, creosote bush, *cucurbita pepo, cupressus sempervirens, curcuma domestica, curcuma longa*, curcumin, curly dock, cusparia febrifuga, cusparia trifoliata, cuspidatum, custard apple, *cyamopsis tetragonolobus*, cyanocobalamin, *cymbopogon* spp., cynara scolymus, *cyperus* articulatus, cypress, cypripedium acaule, cypripedium calceolus, cystadane, cytisus scoparius, daio-kanzo-to, daisy, damiana, dandelion, dangshen (or danshen), date palm, *datura meteloides, datura sauveolens, datura* stramonium, datura wrightii, *daucus* carota, deadly nightshade, deanol, deer velvet, desert parsley, devil's claw, devil's club, di huang, diente de león, diet, macrobiotic, dietary fiber, dietary saccharides, digitalis, dill, dioscorea communis, dioscorea villosa L., diviner's sage, dogwood, *dolichos pruriens*, dolomite, dong quai, D-pantothenic acid, D-phenylalanine, dromaius novaehollandiae, drosera, dumontiaceae, dutchman's pipe, eastern hemlock, echinacea, echinacea angustifolia, echinacea purpurea, echium, elderberry, elecampane, electro colloidal silver, elemental iron, elettaria cardamomum, *eleusine indica*, elletaria cardamomum, elymus repens, emu oil, enebrina, english chamomile, english ivy, english walnut, english yew, ephedra, EGCG (Epigallocatechin gallate), epilobium angustifolium, epilobium parviflorum, epimedium grandiflorum, equinácea, equisetum arvense L., ergocalciferol, eriodictyon californicum, erythroxylum vacciniifolium, eschscholzia californica, escoba negra, espirulina, Essiac®, estevia, eucalyptus oil, euforbio, eufrasia, *eugenia* aromatica, eupatorium perfoliatum, *euphorbia*, euphorbiaceae, euphrasia officinalis, european cranberry, euterpe oleracea, evening primrose oil, evodia rutecarpa, eyebright, *fagopyrum* esculentum, fennel (foeniculum vulgare mill.), fenugreek, fermented milk, ferula assafoetida, feverfew, fucus *carica*, fucus inspida, fig, filipendula ulmaria, fireweed, flaxseed and flaxseed oil, fleet phospho-soda, fleet enema, Flor-Essence®, fly agaric, fo-ti, foxglove, *fragaria, fragaria* vesca, frambuesa, frangula purshiana, frankincense, fraxinus, french rose, friar's cap, fructus barbarum, fucus vesiculosus, fuzheng jiedu tang, gallic acid, galanga, galanthus, galipea officinalis, galium odoratum, gallium aparine, gambierdiscus toxicus, *ganoderma lucidum, garcinia cambogia, garcinia mangostana, garcinia*, ácido hydroxicítrico, garlic, garra del diablo (harpagophytum procumbens), gelatin, gelidiella acerosa, gelsemium, genistein, gentian, gentian violet, geranium maculatum, german chamomile, germander, germanio, germanium, germanium sesquioxide, germinated barley foodstuffs, giant knotweed, gimnema, gentian, ginger, ginkgo, ginseng, *glechoma hederacea*, globe artichoke, glycine soja, glycyrrhiza glabra, gobi, goji, goldenrod, goldenseal, goniopora spp., goosegrass, gossypol, gotu kola, gotu kola y fracción triterpénica total de lacentella asiática (TTFCA), gou qi (chinese wolfberry), gramilla, granada, grape seed extract, grapefruit, grass pea, graviola, greater celandine, greater galangal, green hellebore, green tea, griffonia, *grifola frondosa*, grindelia, grindelia camporum, ground ivy, guar gum, guarana, guayule, guelder rose, guggals, guggul, gum acacia, gum arabic, gumweed, guru nut, *gymnema sylvestre*, gynostemma pentaphyllum, hamamelis, hange koboku-to, haritaki, harpagophytum procumbens, hashish, hawthorn, hazelnut, hedeoma pulegioides L., hedera helix, *helianthus annuus*, hellebore, hemlock, hemp seed oil, hepatica, heracleum maximum, hesperidin, hibiscus, hiedra terrestre, hierba carmín, hierba de cabra en celo (epimedium grandiflorum), hierba de limón (lemon grass), hierba de san juan (hypericum perforatum L.), hierba de trigo (*triticum aestivum*), high bush cranberry, hippophae rhamnoides, holy basil, hochu-ekki-to, honey, honeysuckle, hongo maitake, *hoodia gordonii, hordeum vulgare*, horehound, horny goat weed, horse chestnut, horse chestnut seed extract, horse heal, horseradish, horsetail, hou po (magnolia bark), hoxsey formula, huang qi, huang-teng ken, *humulus lupulus* L., huperzia serrata, huperzine A, hyaluronic acid, hydrangea arborescens, hydrastis canadensis, hydrazine sulfate, hydrocotyle asiatica, hydrilla, *hypericum* perforatum, hypoxis hemerocallidea, hypoxis rooperi, hyssopus officinalis, ignacia (or ignatia), illicium verum, impatiens biflora, impatiens pallida, indian bael, indian barberry, indian fig, indian licorice, indian mulberry, indian poke, indian snakeroot, indian tobacco, inula campana, inula helenium, ipecac, *ipomoea* orizabensis, ipriflavone, iris versicolor, isatis indigotica, iscador, isphagula, ivy, jackfruit, jamaican quassia, japanese yew, japanese sophora, jasmine, jengibre, jequirity, jervine alkaloids, jewelweed, jianpi wenshen recipe, jiaogulan, jimson weed, jointed flatsedge, jojoba, joshua tree, juglans regia, juniper, Kan Jang®, karaya gum, karkada, katuka, kale, kava (piper methysticum), kefir, kelp, khat (catha edulis), khella (ammi visnaga, also known as khellin), kinetin, kiwi, kiwifruit, klamath weed, kola nut, korean red ginseng, krebiozen, krestin, krill oil, kudzu, labrador tea, lactalbumin, *lactobacillus acidophilus, lactobacillus casei, lactobacillus GG, lactobacillus plantarum, lactobacillus reuteri, lactobacillus* sporogenes, lactobacilo acidófilo, lactoferrin, ladies mantle, lady's slipper, laetrile, lagerstroemia speciosa L., larch arabinogalactan, larix, larrea divaricata, larrea tridentata, *lathyrus*, laurus nobilis, laurus *persea*, lavender, lecithin, ledum groenlandicum, ledum latifolium, ledum palustre, legume, lei gong teng, lemon balm, lemongrass, lentinan, lentinula edodes, *lentinus edodes*, lentisco, leonurus cardiaca, *lepidium meyenii, lepidium* peruvianum chacón, lesser celandine, lesser galangal, lessertia frutescens, levisticum officinale, levoglutamide, lichen, licorice, lignans, *ligustrum*, lime, lime flower, linden, lingonberry, linseed oil, *linum* usitatissimum, lipase, lirio azul, lirio de agua blanco (nymphaea odorata), liverwort, L-norvaline, lobelia inflata, locust bean, lomatium, lomatium dissectum, long pepper, lonicera spp., lophosphora spp., lophosphora williamsii, lorenzo's oil, lotus, lousewort, lovage, lucky nut, lúpulo, lutein, luteinai, *lycopersicon esculentum, lycopodium clavatum, lycopodium* serrata, lycopus americanus, lycopus europaeus, lycopus lucidus, lycopus virginicus, lysichiton americanu, ma huang, maca (lepidium peruvianum chacón), macrobiotic diet, madagascar jewel, madder (rubia tinctorum), maeng lak kha, magic mint, magnolia, magnolia and pinelliae formula, mahonia, maidenhair tree, maitake mushroom, malpidnia glabra, malpighia glabra, malpighia punicifolia, *malus* sylvestris, maltas malvavisco, mangaresa, mandarin, mangosteen, manto de nuestra señora (alchemilla vulgaris), manzanilla, MAP30, maranta arundinacea, maria pastora, marigold, marijuana, marrubio blanco, marrubium vulgare, marsh tea, marshmallow, marshmallow root, mastic (psitacia lentiscus), matricaria recutita, mauby bark, MCP (modified citrus pectin), meadowsweet, *medicago sativa* L., melaleuca alternifolia, melaleuca leucadendron, melaleuca quinquenervia, melatonin, *melissa officinalis*, menaquinones, *mentha* pulegium L., *mentha* x piperita L., menthol, mexican scammony root, mezereon, microcrystalline cellulose, microcrystalline hydroxyapatite, milenrama, milk bush, milk thistle, mistletoe, modified citrus pectin, *momordica charantia* L. curcurbitaceae, *momordica* grosvenori, monacolin K, monascus purpureus, monkshood, *morinda citrifolia, morinda* officinalis, moringa, moms nigra, motherwort, mountain balm, moutan, MSM (Methylsulfonylmethane), mucuna pruriens, mugwort, muira puama, mulberry, mullein, musk seed, mustard, myrcia, myrica cerifera, myrrh, narrowleaf plantain, nasturtium officinale, neem, nelumbo nucifera, neovastat, *nepeta cataria*, nerium oleander, nettle, nexrutine, *nicotiana glauca, nicotiana tabacum*, nigella sativa, noni (*morinda citrifolia*), nopal, northern prickly ash, norvaline, nuez de betel (*areca catechu* L.), nutmeg, nux vomica, nymphaea odorata, oak bark, oak moss, oat beta-glucan, oat bran/straw, oat, ocimum basilicum, ocimum sanctum L., oenothera biennis L., okra, old man's beard, *olea europaea*, oleander, olibanum, olive leaf, olive oil, olmo resbaladizo, oplopanax horridus, opuntia streptacantha, orbignya phalerata, oregano, oregon grape, *origanum* vulgare, ornithine, ovoester, oxerutin, oxykrinin, ox bile extract, pacific yew, pagoda tree, palm oil, palma enana americana (serenoa repens), pamabrom, *panax ginseng, papaver rhoeas, parietaria officinalis*, parsley, parsnip, parthenium argentatum, parthenolide, pasiflora, passion flower, pastinaca, pastinaca sativa, pau d'arco, paullinia cupana, pausinystalia yohimbe, PC-SPES, peanut oil, pectin, pedicularis, pedra hume caá (myrcia salicifolia), pellitory-of-the-wall, pencil tree, pennyroyal (mentha pulegium), peony, peppermint, peppermint oil, *perilla frutescens*, periwinkle, *persea americana*, petadolex, petasita, petasites hybridus, petty spurge, peumus boldus, peyote, phaseolamin (white kidney bean), *phaseolus vulgaris varieties, phoenix* dactylifera, phoradendron leucarpum, phyllanthus, physalis somnifera, phyto-1, *phytolacca americana*, picraena excelsa, picrasma excelsa, picrorhiza kurroa, pill-bearing spurge, pimenta dioica, pimpinella anisum, pine bark extract, pine pollen, *pinus maritima, pinus* palustris, piper methysticum, piper nigrum, pistacia lentiscus, plant stanol ester, *plantago coronopus, plantago isphagula, plantago lanceolata, plantago ovata*, pleurisy, podophyllum hexandrum, podophyllum peltatum, poinsettia, poison ivy, poke root, pokeweed, poleo americano, policosanol, *polygonum cuspidatum, polygonum* multiflorum, polypodium leucotomos extract and anapsos, pomegranate, *populus*, poppy, precatory bean, prickly ash, prickly pear cactus, primula officinalis, primula veris, probeta, promensil, propagermanium, propolis, prunella vulgaris, prunus africanum, *prunus amygdalus*, prunus amygdalus dulcis, prunus armeniaca, prunus armeniaca L., psyllium, ptychopetalum olacoides, pueraria lobata, pueraria montana var., puerarin, puerto rican cherry, pulegone, pulsatilla, pumpkin, pumpkin seed oil, punica granatum, purple viper bugloss, pycnogenol, pygeum bark, pyres communis, pyruvate, qing hao, qinghao, qinghaosu, quack grass, quaker bonnet, quaker buttons, quaking aspen, quassia, queen anne's lace, queen of fruits (mangosteen fruts), queen of the meadow, queen's crape myrtle, *quercus alba, quercus cortex, quercus* marina, quick-in-the-hand (jewelweed), quimsa-kuchu, quinoa, quinsu-cucho, quitch grass, rabdosia rubescens, radium weed, radix angelica sinensis, ranunculus bulbosus, ranunculus ficaria, rapeseed oil, raspberry, rauvolfia serpentine, red algae, red clover, red palm oil, red sorrell, red stinkwood, red yeast rice, regaliz, rehmannia, rehmannia glutinosa, reina de los prados (spiraea ulmaria), reishi mushroom, rennet, rhamnus purshiana, rheum officinale, rheum palmatum, rhodiola, rhodiola rosea, rhododendron tomentosum, rhubarb, *rhus tox, ribes* nigrum, rice bran oil, ricola, roble blanco, roman chamomile, romero, rooibos, *rosa* canina, rosary pea, rose haw, rose hip, rose laurel, roselle, rosemary, *rosmarinus officinalis* L., royal jelly, rhubarb, *rubus fructicosus*, rubus idaeus, *rubus* villosus, ruibarbo, rumalon, rumex crispus, ruscus aculeatus, ruta graveolens, rutin, rye grass, sabal serrulata, sábila, *saccaromyces cerevisiae, saccharomyces boulardii, saccharomyces* thermophilus, safflower, sage, saiboku-to, saiko-keishi-to, Salba®, *salix alba, salix* spp., salvia divinorum, salvia hispanica, salvia lavandulaefolia, salvia lavandulifolia, salvia miltiorrhiza, *salvia officinalis*, samambaia, sambucas nigra, sandalwood, sanguinaria canadensis, sanguinarine, santalum album, sarsaparilla, sassafras, sauco berry (*sambucus nigra*), saw palmetto, schisandra chinensis, schizandra berry, schizandrae, schizopeta, scopolamine, scotch broom, scullcap, *scutellaria baicalensis, scutellaria barbata, scutellaria* lateriflora, sea buckthorn, seaweed, bladderwrack, *secale cereale*, secretin, seer sage, sehydrin, sea cucumber, selagine, senna, serine, serenoa repens, sesame oil, seso vegetal, shakuyaku-kanzo-to, shallot, shark cartilage, sheng dihuang, shepherd's purse, shepherd's purse, shiitake mushroom, shikonin, sho seiryu to, sho-saiko-to, shuang huang lian, siamese ginger, silka deer, silver birch, silver protein, silymarin, simmondsia chinensis, sisal, skunk cabbage, slippery elm, smilax spp., smokeless tobacco, snakeroot, snowball bush, soja, solidago virgaurea, sophora, *sor-

*ghum vulgare*, sorrel, sour cherry, sour orange juice, soy, soy bean extract, soy bran, soy protein, soy sprouts, soybean oil, sparteine, spinach, spirogermanium, spirulina, spurge olive, squill, st. ignatius bean, st. john's bread, st. john's wort, stachys betonica, stachys officinalis, star anise, *stellaria media*, sterculia urens, stevia, stickleburr, stinging nettle, stinking goosefoot, strychnos ignatii, strychnos nux-vomica, styphnolobium japonicum, substance x, sulfato de condroitina, suma (pfaffia paniculata), sunflower seed oil, sutherlandia frutescens, swamp hellebore, sweet almond, sweet annie, sweet basil, sweet cherry, sweet orange, sweet root, sweet woodruff, sweet wormwood, sweetflag, symphytum, symphytum officinale, symplocarpus foetidus, tadenan, tamanu, tamarind, tamarindus indica L., tamus communis, tanacetum parthenium, tanacetum vulgare, tangerine, tansy, taraxacum officinale, taurine, tea tree oil, tejo, terminalia, teucrium chamaedrys, *theobroma cacao*, thevetia peruviana, *thuja* occidentalis, thunder god vine, thyme (*thymus vulgaris*), tibetan goji berry, tilofora, toki-shakuyaku-san, toxicodendron radicans (eastern poison ivy), tragacanth, tree tobacco, trembling aspen, tribulus terrestris, trichilia catigua, trierucate oil, *trifolium pratense*, trigonella foenum-graecum, trigonella foenum-graecum L. leguminosae, trimethylethanolamine, tripterygium wilfordii, *triticum aestivum, tsuga canadensis*, TTFCA (total triterpenic fraction of centella asiatica), tuftsin, tulsi holy basil, turkey tail mushroom, turmeric, turnera aphrodisiaca, turnera diffusa, turpentine oil, tussilago farfara, tylophora, tylophora indica, Ukrain™, ulmus rubra/ulmus fulva, umbrella arum, uncaria guianensis, uncaria tomentosa, urginea maritima, *urtica dioica*, usnea barbata, uva ursi, *vaccinium angustifolium, vaccinium macrocarpon, vaccinium* myrtillus anthocyanoside, *vaccinium vitis*-idaea, valerian, velvet deer antler, velvet flower, velvetleaf, veratrum viride, verbascum thapsus, verbena, vervain, vetchling, vetiver (chrysopogon zizanioides), viburnum opulus, viburnum prunifolium, vinagre de sidra de manzana, vinca minor, vinpocetine, viper's bugloss, virginia's herbal E-Tonic™, *viscum album* L., vitex agnus-castus, *vitis vinifera*, vulvaria, *wasabia* japonica, water hemlock, watercress, wheatgrass, wheat bran/grass, wheat germ, wheat sprouts, whey protein, white horehound, white mallow, white oak, white pepper, white sandalwood, white tea, white water lily, wild arrach, wild carrot, wild cherry, wild ginger, wild indigo, wild marjoram, wild rosemary, wild yam, willow bark, witch hazel, withania somnifera, wintergreen, wood betony, wolfberry, wormwood, Xango®, xanthan gum, *xanthomonas campestris*, xhoba, xi yang shen, xi zhang hu huang lian, xian cao, xian ling pi, xianxao, xiao qing long tang, xiao-chai-hutang, xu ku cao, xue zhi kang, yadake, yagona, yam, yamabushitake mushroom, yang-mei, yangona, yaqona, yarrow, yashti-madhu, yashti-madhuka, yavatikta, yege, yellow astringent, yellow bark, yellow beeswax, yellow beet, yellow broom, yellow dock, yellow ginseng, yellow horse, yellow indian paint, yellow indigo, yellow jasmine, yellow oleander, yellow poppy, yellow puccoon, yellow root, yellow sandalwood, yellow saunders, yellow starwort, yemen myrrh, yerba dulce, yerba mate, yerba santa, yew, yi zhu, yin yang huo, yinhsing, yodo, yogaraj guggul gum resin, yohimbe bark extract (pausinystalia yohimbe), yongona, yuan hu suo, yucca, yucca aloifolia, yucca angustifolia, yucca arborescens, yucca breifolia, yucca filamentosa, yucca glauca, yucca schidigera, yucca whipplei, yun zhi, zanthoxylum americanum, zapatilla de dama, *zea mays*, Zemaphyte®, zingiber officinale roscoe, or ZMA™. The composition may be used as nutritional supplement, dietary supplement, food supplement, or as a food additive. The composition may be manufactured as a tablet, capsule, liquid, lyophilized powder, powder, crystalline, aerosol, liquid impregnated onto a dermal patch, ointment, or suppository.

In a related embodiment, the magnesium-counter ion composition may also contain other nutritional ingredients including, without limitation, calcium-containing materials such as calcium carbonate, stannol esters, hydroxycitric acid, vitamins, minerals, herbals, spices and mixtures thereof. Examples of vitamins that are available as additional ingredients include, but are not limited to, vitamin A (retinol), vitamin D (cholecalciferol), vitamin E group (alpha-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final product is dependent on the particular vitamin. Examples of minerals that are available as additional ingredients include, but are not limited to, calcium, phosphorus, iron, zinc, iodine, selenium, potassium, copper, manganese, molybdenum and mixtures thereof. As is the case with vitamins, the amount of mineral or minerals present in the final product is dependent on the particular mineral. It will be clear to one of skill in the art that the present list of additional neutriceutical components are provided by way of example only, and are not intended to be limiting.

In addition to oral dosage forms, the compositions of the present invention can be administered to a subject by any available and effective delivery systems. Such delivery systems include, but are not limited to, parenteral, transdermal, intranasal, sublingual, transmucosal, intra-arterial, or intradermal modes of administration in dosage unit formulations containing conventional nontoxic physiologically acceptable carriers, adjuvants, and vehicles as desired, such as a depot or a controlled release formulation. Depending on the route of administration, the magnesium composition of the present invention may be formulated as a suppository, lotion, patch, or device (e.g., a subdermally implantable delivery device or an inhalation pump). The compositions may be optimized for particular types of delivery.

In some embodiments of the present invention, magnesium and threonate are delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable excipients as set out above. Preferably the compositions of the present invention are administered by the oral, intranasal or respiratory route for local or systemic effect. Compositions in acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

In some embodiments, for example, the composition may be delivered intranasally to the cribriform plate rather than by inhalation to enable transfer of the active agents through the olfactory passages into the CNS and reducing the systemic administration. Devices commonly used for this route of administration are included in U.S. Pat. No. 6,715,485, entitled "Nasal delivery device." Compositions delivered via this route may enable increased CNS dosing or reduced total body burden reducing systemic toxicity risks associated with certain compositions.

The composition may optionally be formulated for delivery in a vessel that provides for continuous long-term delivery, e.g., for delivery up to 30 days, 60 days, 90 days, 180 days, or one year. For example the vessel can be provided in a biocompatible material such as titanium. Long-term delivery formulations are particularly useful in subjects with chronic conditions, for assuring improved patient compliance, and for enhancing the stability of the compositions.

According to another embodiment, the composition of the invention is a liquid or semi liquid comprising at least 20 mg/L magnesium, or at least 40 mg/L magnesium. In some embodiments, the composition of the invention is a liquid or semi liquid comprising at least 5 mg/L magnesium, at least 10 mg/L magnesium, at least 20 mg/L magnesium, at least 30 mg/L magnesium, at least 40 mg/L magnesium, at least 50 mg/L magnesium, at least 60 mg/L magnesium, at least 70 mg/L magnesium, at least 80 mg/L magnesium, at least 90 mg/L magnesium, or at least 100 mg/L magnesium.

Alternatively, the compositions of the present invention may be administered transdermally. Preparation for delivery in a transdermal patch can be performed using methods also known in the art, including those described generally in, e.g., U.S. Pat. Nos. 5,186,938 and 6,183,770, 4,861,800, 6,743,211, 6,945,952, 4,284,444, and WO 89/09051, incorporated herein by reference in their entireties. A patch is a particularly useful embodiment with active agents having absorption problems. Patches can be made to control the release of skin-permeable active ingredients over a 12 hour, 24 hour, 3 day, and 7 day period. In one example, a 2-fold daily excess of magnesium threonate is placed in a non-volatile fluid. A preferred release can be from 12 to 72 hours.

In some embodiments, for example, the composition may be delivered via intranasal, buccal, or sublingual routes to the brain rather than by inhalation to enable transfer of the active agents through the olfactory passages into the CNS and reducing the systemic administration. Devices commonly used for this route of administration are included in U.S. Pat. No. 6,715,485, entitled "Nasal delivery device." Compositions delivered via this route may enable increased CNS dosing or reduced total body burden reducing systemic toxicity risks, e.g., diarrhea.

Preparation of a compositions for delivery in a subdermally implantable device can be performed using methods known in the art, such as those described in, e.g., U.S. Pat. Nos. 3,992,518; 5,660,848; and 5,756,115. Additional methods for making modified release formulations are described in, e.g., U.S. Pat. Nos. 5,422,123, 5,601,845, 5,912,013, and 6,194,000, all of which are hereby incorporated by reference.

II. Uses

The present invention provides methods of using the compositions disclosed herein. In some embodiments, such uses comprise administering the oral dosage forms of the present invention to provide a variety of health benefits. Such a composition may comprise at least one magnesium-counter ion compound. A magnesium-counter ion composition described herein may be useful for any of a variety of applications and purposes described herein, such as maintaining, enhancing, and/or improving health, nutrition, and/or another condition of a subject, and/or cognitive, learning, and/or memory function, for example. Magnesium deficit may lead to or may be associated with many pathological symptoms, such as loss of appetite, nausea, vomiting, fatigue, seizures, abnormal heart rhythms, diabetes, and/or cardiovascular disease, for example. According to several studies, magnesium deficit may lead to or may be associated with attention deficit hyperactivity disorder (ADHD) in children and symptoms associated therewith (Kozielec et al., Magnes. Res. 10(2), 143-148 (1997) and Mousain-Bosc et al., Magnes. Res. 19(1), 46-52 (2006)). A magnesium-counter ion composition described herein may be useful for administration to a subject presenting magnesium deficiency, mild cognitive impairment, Alzheimer's disease, attention deficit hyperactivity disorder, ALS, Parkinson's disease, diabetes, migraine, anxiety disorder, mood disorder, and/or hypertension, merely by way of example.

Magnesium is an essential mineral in the human body and plays a role in numerous physiological functions. Yet, it is generally recognized that at least half of the people in the industrialized world do not get sufficient magnesium from their diets. Several diseases, such as diabetes and Alzheimer's disease (AD), are associated with magnesium deficit. Therefore, there is a need for magnesium supplementation. The recommended daily allowance (RDA) for magnesium is about 400 mg for adults. By assuming that people get 40-50% of the required magnesium from diet, the recommended amount of magnesium supplement has generally been about 200-250 mg per day for adults. There are numerous magnesium compounds that have been used as magnesium supplements. These compounds include magnesium oxide, magnesium citrate, magnesium sulfate, magnesium chloride, magnesium gluconate, magnesium lactate, magnesium pidolate and magnesium diglycinate, for example. At least for nutritional purpose, the recommended amount of magnesium supplementation for most commercial magnesium supplements is about the same (i.e., about 250 mg magnesium per day), regardless of the bioavailability of the magnesium compound and the individual's kidney function to retain the amount of the absorbed magnesium. Some magnesium supplement suppliers have recommended higher daily magnesium intake for their products, again, without considering an individual's kidney function for magnesium retention. Similar to magnesium deficit, an excessive amount of magnesium in the body (hypermagnesemia) may also lead to health problems, such as neuromuscular depression, hypotension, cardiac arrythmias and respiratory paralysis. Thus, it is important to have one's blood magnesium level stay within the normal range. Disclosed herein is a novel method for controlling the magnesium level to a particular region of the normal range. In some aspects of the invention, this method also offers particular health advantages, such as increased memory capabilities, increased lifespan, decreased depression, and decreased symptoms of neurological disorders, including AD.

In addition to nutritional use, magnesium supplements have been used for treating type 2 diabetes. In one study, diabetic patients were treated with nearly 1 g of magnesium daily using magnesium oxide for 1 month (de Lordes Lima, et al., *Diabetes Care.* 21: 682-6 (1998)). The treatment increased the serum magnesium level of the patients by about 10% but with only minor improvement in metabolic control. In another study, diabetic patients were treated with 720 mg/day of magnesium for three months. Similarly, the blood magnesium levels of the patients were raised by about 10% on average (Eibl, et al., *Diabetes Care.* 21: 2031-2 (1995)). However, the metabolic control of the patients, as assessed by their HbA1c levels, had no improvement.

Magnesium ion has been reported to be generally useful for treatment of dementia (e.g., U.S. Pat. No. 4,985,256, entitled "Methods for diagnosing, monitoring and controlling the onset and progression of certain dementias and impeding memory loss or improving impairment of memory"). Landfield and Morgan showed that young (9-month old) and aged (25-month old) rats fed food containing 2% magnesium oxide for 8 days had shown some sign of improvement of cognitive function (Landfield and Morgan, Brain Research, 322:167-171 (1984)). However, the gain in cognitive function was transient and at the cost of diarrhea and weight loss to the animals. In fact, the side-effect was so severe the researchers had to use an alternating feeding schedule by having the animals on the high Mg diet for 4 days, followed by a regular diet for two days and then back to the high Mg diet for another 4 days.

Magnesium compounds may also be used to affect bone density. Bone density disorders, including but not limited to osteoporosis, may be treated by supplementation with magnesium compounds of the present invention. Subjects may be treated to ameliorate the effects of low bone density or as prophylaxis against lost bone density. Bone density may be measured by any means known in the art, including, but not limited to, dual energy X-ray absorptiometry (DEXA), ultrasound, quantitative computed tomography, single energy absorptiometry, magnetic resonance imaging, measuring metacarpal width, and hand X-ray analysis.

As mentioned above, a magnesium-counter ion composition and/or a method described herein are useful for various purposes, such as maintaining, enhancing, and/or improving health, nutrition, and/or another condition of a subject, and/or cognitive, learning, and/or memory function, for example. Examples of such a condition of a subject include magnesium deficiency, mild cognitive impairment, Alzheimer's disease, Huntingdon's disease, autism, schizophrenia, cognitive decline as secondary effect of disease or medical treatment (HIV disease, cancer, chemotherapy), depression, dementia, attention deficit hyperactivity disorder, Amyotrophic lateral sclerosis (ALS), Parkinson's disease, diabetes, cardiovascular disease (e.g., hypertension), glaucoma, migraine, anxiety, mood, and hypertension, merely by way of example. Magnesium supplementation may also be useful in maintaining, enhancing, and/or improving conditions which may result in loss of body magnesium, including, but not limited to, alcoholism, anorexia, bulemia, metabolic syndromes, and poor nutrition. Any such condition may be deemed or defined as a physiological, psychiatric, psychological, or medical condition or disorder, for example. Generally, the term "subject" may refer to any animal. Examples of such animals include, but are not limited to, cold-blooded animals, warm-blooded animals, mammals, domesticated mammals, primates, humans, and individuals or a patient to whom a composition is to be administered for experimental, diagnostic, nutritional, and/or therapeutic purposes. A subject or patient may be a subject or patient of normal, good, or excellent health, mood, cognitive, and/or nutritional status, or of compromised health, mood, cognitive, and/or nutritional status, including of abnormal, poor, damaged, unhealthy, impaired, diseased, and/or nutritionally deficient status. The subject may be of any age, including advanced age.

Generally, the term "cognition" may refer to a process of obtaining, organizing, understanding, processing, and/or using information or knowledge. Generally, enhancing cognitive function refers to enhancing any aspect of such a process, such as learning, the performance of mental operations, the storage, retrieval, and/or use of information and/or thoughts, memory, and/or preventing a decline of a subject's cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

Generally, the term "concurrent administration" in reference to two or more subjects of administration for administration to a subject body, such as components, agents, substances, materials, compositions, and/or the like, refers to administration performed using dose(s) and time interval(s) such that the subjects of administration are present together within the subject body, or at a site of action in the subject body, over a time interval in less than de minimus quantities. The time interval may be any suitable time interval, such as an appropriate interval of minutes, hours, days, or weeks, for example. The subjects of administration may be administered together, such as parts of a single composition, for example, or otherwise. The subjects of administration may be administered substantially simultaneously (such as within less than or equal to about 5 minutes, about 3 minutes, or about 1 minute, of one another, for example) or within a short time of one another (such as within less than or equal to about 1 hour, 30 minutes, or 10 minutes, or within more than about 5 minutes up to about 1 hour, of one another, for example). The subjects of administration so administered may be considered to have been administered at substantially the same time. One of ordinary skill in the art will be able to determine appropriate dose(s) and time interval(s) for administration of subjects of administration to a subject body so that same will be present at more than de minimus levels within the subject body and/or at effective concentrations within the subject body. When the subjects of administration are concurrently administered to a subject body, any such subject of administration may be in an effective amount that is less than an effective amount that might be used were it administered alone. The term "effective amount," which is further described herein, encompasses both this lesser effective amount and the usual effective amount, and indeed, any amount that is effective to elicit a particular condition, effect, and/or response. As such, a dose of any such subject of concurrent administration may be less than that which might be used were it administered alone. One or more effect(s) of any such subject(s) of administration may be additive or synergistic. Any such subject(s) of administration may be administered more than one time.

Generally, the term "effective amount" in reference to an active agent refers to the amount of the active agent sufficient to elicit a particular biological condition, effect, and/or response. The absolute amount of a particular agent that is effective in this manner may vary depending on various factors, such as the desired biological endpoint, the agent itself, the subject or targeted part thereof, and/or the like, for example. An effective amount of an active agent may be administered in a single dose or in multiple doses. Examples of a biological condition, effect, or response that may result from an effective amount of an active agent include a maintaining and/or improving of a subject's performance of a task involving or associated with cognitive function, a maintaining and/or improving of a subject's performance in a test that measures something relating to or associated with cognitive function, a maintaining and/or improving (slowing, for example) of a rate of decline in cognitive function, and/or the like, for example. A component may be described herein as having at least an effective amount, or at least an amount effective, such as that associated with a particular goal or purpose, such as any described herein.

Generally, the term "physiologically acceptable," or "pharmaceutically acceptable," means biologically or pharmacologically compatible for in vivo use in animals or humans, e.g., approved by a regulatory agency of the Federal or a state government or listed in the U.S. Pharmacopeia or other generally recognized pharmacopeia for use in animals, and more particularly in humans.

As used herein, the term "treat", in all its verb forms, included to relieve or alleviate at least one symptom of a disorder in a subject, the disorder including, e.g., pain, Alzheimer's disease, vascular dementia, or Parkinson's disease. The term "treat" may mean to relieve or alleviate the intensity and/or duration of a manifestation of a disorder experienced by a subject in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognition. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the dementia is associated with a CNS disorder, including without limitation neurodegenerative diseases such as Alzheimer's disease (AD), Down's Syndrome and cerebrovascular dementia (VaD). The term "treatment" includes the act of "treating" as defined above.

The term "dose proportional" as used herein refers to the relationship between the dose of an active ingredient and its bioavailability. For example, dose proportionality exists if twice as much of the same composition will deliver twice the active ingredient and provide the same bioavailability (e.g., AUC) as one dose of the dosage form. The dose proportionality of the present invention applies to a wide range of doses as discussed in detail herein.

Generally, the term "elemental magnesium" as used in connection with a magnesium-counter ion compound described herein, may refer to a total amount of magnesium that is present as free ion and magnesium that is bound with one or more counter ions. In general, such a term is not used to refer to magnesium that may be associated with an agent other than a magnesium-counter ion compound that may be a component of a magnesium-counter ion composition (e.g., a pharmaceutical composition, a dietary supplement composition, a foodstuff supplemented with a magnesium-counter ion compound). A small amount of magnesium may be naturally present in or otherwise associated with such an agent. For example, a fruit juice extract or flavoring agent may comprise an amount of magnesium from that naturally present in the fruit from which it was derived. Generally, the term "elemental magnesium" as used in connection with an magnesium-counter ion compound would not encompass such agent-associated magnesium.

As used herein, the terms "magnesium comprising component" (MCC) and "magnesium-counter ion compound" are used interchangeably, and they are useful for purposes described herein, such as maintaining, enhancing, and/or improving health, nutrition, and/or another condition of a subject, such as magnesium deficiency, diabetes, mood, attention deficit hyperactivity disorder, ALS, Parkinson's disease, anxiety, depression and/or migraine, for example, and/or cognitive, learning, and/or memory function, such as MCI and/or AD, for example.

Magnesium threonate has been shown to have the highest bioavailability in comparison to magnesium compounds commonly used as magnesium supplements. The ability to rapidly and efficiently deliver magnesium from GI track to blood makes the compound an excellent candidate for pharmaceutical applications, such as treating neurological disorders or deficiencies associated with magnesium deficit or those disorders for which magnesium is known to be effective. See U.S. patent application Ser. No. 12/054,373, entitled "Magnesium Compositions, Methods of Using Same, and Associated Technology." For example, magnesium threonate was found to be effective as a memory enhancer in young animals and in treating memory loss associated with aging or Alzheimer's disease (AD) in animals. See U.S. patent application Ser. No. 12/054,373. However, for a composition to be useful as a dietary or nutritional supplement or for enhancing health in general, it should have low side effects and provide health benefits. Unlike a pharmaceutical composition, which may be prescribed by a health professional to a patient with a specific medical condition, a dietary or nutritional supplement may be taken by either a healthy or unhealthy person and typically on a daily basis for a extended period of time, such as several months, several years or even a lifetime. Thus, it is important to provide sufficient data to support the long-term safety and benefit of a dietary/nutritional supplement when the supplement is administered at the effective dosage.

In some embodiments, the present invention provides a method of supplementing magnesium in a subject in need thereof. The subject can be any animal, as described herein. In some embodiments, said subject is a human. Immediate release formulations magnesium threonate (and related compositions) have been show to be useful in a number of settings, including improved cognitive function and synaptic plasticity (U.S. patent application Ser. Nos. 12/054,367 entitled "Magnesium Compositions and Uses Thereof for Cognitive Function" and 12/258,891 entitled the same, treating neurological disorders (U.S. patent application Ser. No. 12/054,384 entitled "Magnesium Compositions and Uses Thereof for Neurological Disorders"), metabolic disorders (U.S. patent application Ser. No. 12/054,374 entitled "Magnesium Compositions and Uses Thereof for Metabolic Disorders"), and increasing lifespan (U.S. patent application Ser. No. 12/054,368, entitled "Magnesium Compositions and Uses Thereof for Increasing Lifespan").

The present invention provides methods to administer the oral dosage forms. In some embodiments, a method of administering an oral dosage form as described herein comprises administering the oral dosage forms to a subject once a day (UID), twice a day (BID), three times a day, four times a day, or more than six times a day. In some embodiments, the oral dosage forms as described herein are administered once a week, twice a week, three times a week, four times a week, five times a week, six times a week, or seven times a week. In some embodiments, the oral dosage forms as described herein are administered once a month, twice a month, times a month, four times a month, five times a month, six times a month, or more than six times a month.

The oral dosage forms as described herein can be used to supplement magnesium in a continuous manner, e.g., over a lifetime. The dosage forms are also useful for providing magnesium over a period of time, e.g., for a period sufficient to treat, control or otherwise benefit a magnesium deficiency. In one embodiment, the present invention provides a method of supplementing magnesium in a subject in need thereof, the method comprising administering an oral dosage form as described herein to said subject at least twice a day for a period of 1 month or longer, 2 months or longer, 3 months or longer, 4 months or longer, 5 months or longer, 6 months or longer, or at least twice a day for a period of one year or longer. In some embodiments, once a day administration is sufficient to provide optimal magnesium supplementation.

Using any regimen of administration, such as those described herein, the present invention provides method of treating a condition related to magnesium deficiency comprising administering to a subject in need thereof any oral dosage form as described herein. For example, the condition can be a neurological disorder, a cardiovascular disorder, or a metabolic disorder. Other conditions which benefit from the present invention include, but are not limited to, magnesium deficiency, mild cognitive impairment, Alzheimer's disease, attention deficit hyperactivity disorder, ALS, Parkinson's disease, diabetes, migraine, anxiety disorder, mood disorder, and/or hypertension. One of skill in the art will appreciate that the oral dosage forms and methods of the present invention can be use to treat any condition that responds favorably to magnesium supplementation.

In other embodiments, oral dosage forms of the present invention are administered to a subject at a dose between about 4 mg elemental magnesium/kg/day to about 8 mg elemental magnesium/kg/day, or between about 2 mg elemental magnesium/kg/day to about 12 mg elemental magnesium/kg/day, or between about 2 mg elemental magnesium/kg/day to about 10 mg elemental magnesium/kg/day, or between about 4 mg elemental magnesium/kg/day to about 12 mg elemental magnesium/kg/day, or between about 6 mg elemental magnesium/kg/day to about 12 mg elemental magnesium/kg/day, or between about 2 mg elemental magnesium/kg/day to about 10 mg elemental magnesium/kg/day, or between about 4 mg elemental magnesium/kg/day to about 10 mg elemental magnesium/kg/day, or between about 6 mg elemental magnesium/kg/day to about 10 mg elemental magnesium/kg/day. The optimal dosage can be dependent on the subject. In some embodiments, the subject is a human. In such embodiment, the dosage can be optimized to treat a condition in a human.

In some embodiments, the oral dosage forms of the present invention is administered to a subject at a dose less than about 2 mg elemental magnesium/kg/day, less than about 4 mg elemental magnesium/kg/day, less than about 6 mg elemental magnesium/kg/day, less than about 8 mg elemental magnesium/kg/day, less than about 10 mg elemental magnesium/kg/day, or less than about 12 mg elemental magnesium/kg/day. In some embodiments, the oral dosage forms of the present invention are administered to a subject at a dose more than about 2 mg elemental magnesium/kg/day, more than about 4 mg elemental magnesium/kg/day, more than about 6 mg elemental magnesium/kg/day, more than about 8 mg elemental magnesium/kg/day, more than about 10 mg elemental magnesium/kg/day, or more than about 12 mg elemental magnesium/kg/day. The optimal dosage can depend on the subject. In some embodiments, the subject is a human. In such an embodiment, the dosage can be optimized to treat a condition in a human.

In some embodiments, the invention provides an oral dosage form comprising magnesium (Mg) and threonate (T), wherein said threonate comprises one or more of a threonate salt or a threonate precursor, wherein said oral dosage form is readily absorbed or retained upon administering to a subject such that at least about 50% of said administered magnesium is absorbed in said subject, or that at least 30% of the magnesium administered to the subject is retained over a period of at least two days when said oral dosage form is administered at a dose of 20 mg/kg/day or higher.

The forms of magnesium described herein are advantageous for their high bioavailability. The schedule of administration and dose of administration can depend on the amount of magnesium that is bioavailable in a subject. In some embodiments, more than about 10%, 20%, 30%, 40%, 50%, 60%, 70%, 80% or more than about 90% of said administered magnesium is absorbed in said subject.

In some embodiments, the amount of magnesium absorbed in the subject is proportional to dosage. For example, the amount of magnesium absorbed can be linearly proportional to the dosage. In some embodiments, the oral dosage form exhibits a dose-proportional increase in absorbed magnesium when administered to a subject in an amount between about 20 mg/kg/day and about 100 mg/kg/day, between about 20 mg/kg/day and about 90 mg/kg/day, or between about 20 mg/kg/day and about 80 mg/kg/day, or between about 20 mg/kg/day and about 70 mg/kg/day, or between about 20 mg/kg/day and about 60 mg/kg/day, or between about 20 mg/kg/day and about 50 mg/kg/day, or between about 30 mg/kg/day and about 100 mg/kg/day, or between about 40 mg/kg/day and about 100 mg/kg/day, or between about 50 mg/kg/day and about 100 mg/kg/day, or between about 60 mg/kg/day and about 100 mg/kg/day, or between about 70 mg/kg/day and about 100 mg/kg/day.

In some embodiments, the dosage form of the present invention has a dissolution rate of magnesium about 40-80% within about 6 to 10 hours.

Magnesium compositions have the potential to cause diarrhea. Indeed, magnesium compounds have been commonly used as laxatives, and magnesium-hydroxide is a commonly known over-the-counter laxative and is the active ingredient in Phillips' Milk of Magnesia. Moreover, Chinese Patent 1200366A discloses that magnesium threonate is useful as a laxative. However, the present invention shows that magnesium threonate has the least tendency to cause diarrhea among a number of commonly used magnesium supplement compounds. See I.Example 2 and FIG. 1.

The incidence of diarrhea can be estimated by providing a dosage of magnesium threonate or a precursor thereof to a group of test animals, e.g., rat or mice, and assessing the incidence of diarrhea in the group of animals. In one embodiment, the present invention provides an oral dosage form comprising between about 30 mg to 2000 mg magnesium (Mg), wherein said oral dosage form is a controlled release formulation, and wherein upon administering said oral dosage form to a subject a dosage of greater than 40 mg/day yields an incidence of diarrhea of less than 20%. The incidence can depend on the particular subject, the body weight of the subject, and the bioavailability of the magnesium provided. For example, the incidence of diarrhea in mice fed a water solution containing magnesium threonate can depend on, e.g., the strain, age or sex of the mice.

In some embodiments, the oral dosage forms of the present invention provides for an incidence of diarrhea of less than 50%, 40%, 30%, 20%, 10%, or less than about 5% when administered to at a dosage of greater than 80 mg/day.

In some embodiments, the incidence of diarrhea is less than 20% when administered to a subject at a dosage of greater than 40 mg/day for at least about 2, 3, 4, 5, 6 days. In some embodiments, the incidence of diarrhea is less than 20% when administered to a subject at a dosage of greater than 40 mg/day for at least about one week, or two weeks, or three weeks or more. In some embodiments, the incidence of diarrhea is less than 20% when administered to a subject at a dosage of greater than 40 mg/day for at least about one month.

Figure 2:
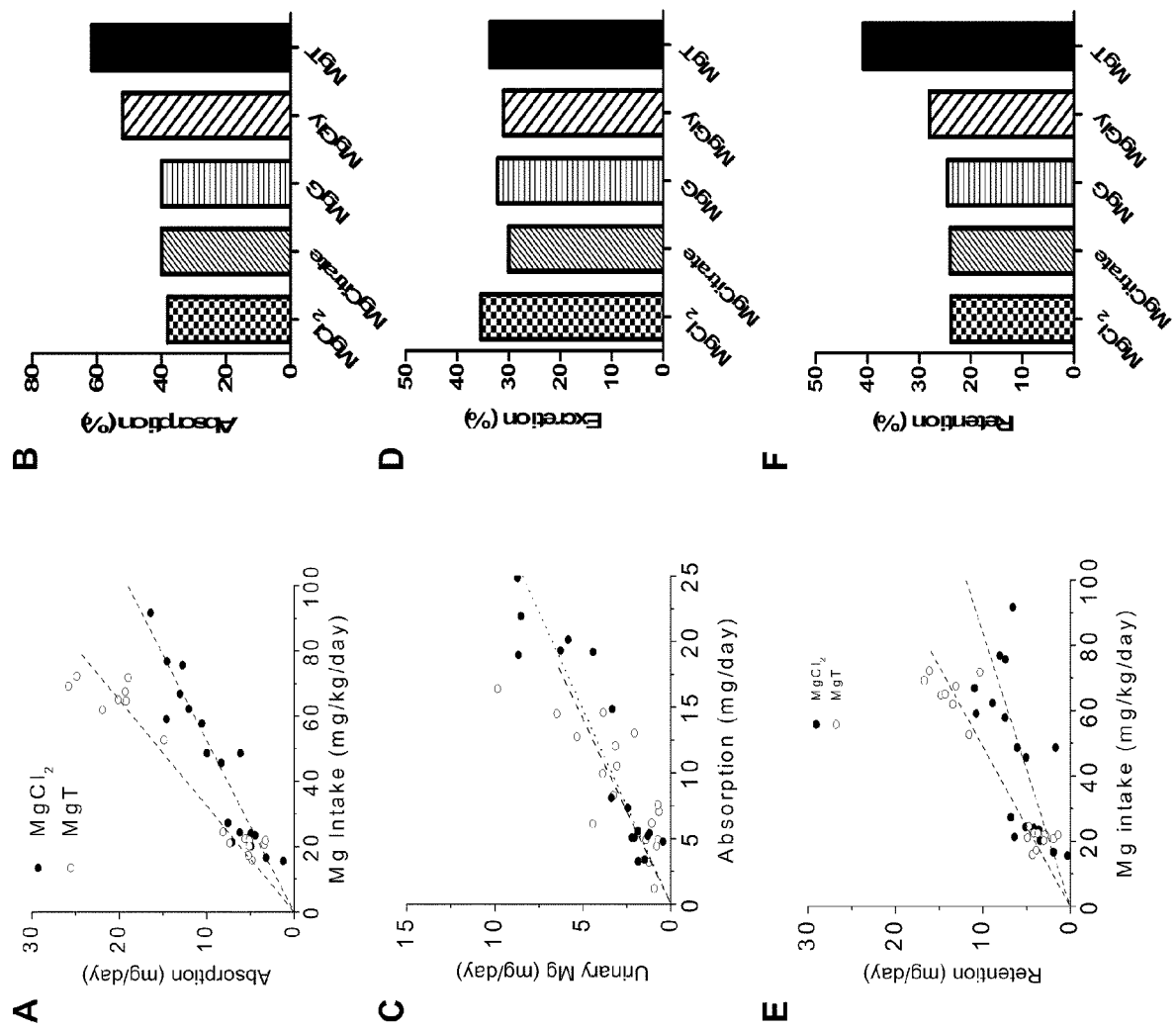
FIG. 2 illustrates a series of plots showing the absorption, reabsorption and retention rate of different magnesium preparations. The preparations included magnesium chloride ($MgCl_2$); magnesium citrate (MgCltrate); magnesium gluconate (MgG); magnesium glycinate (MgGly); and magnesium threonate (MgT).
Figure 3:
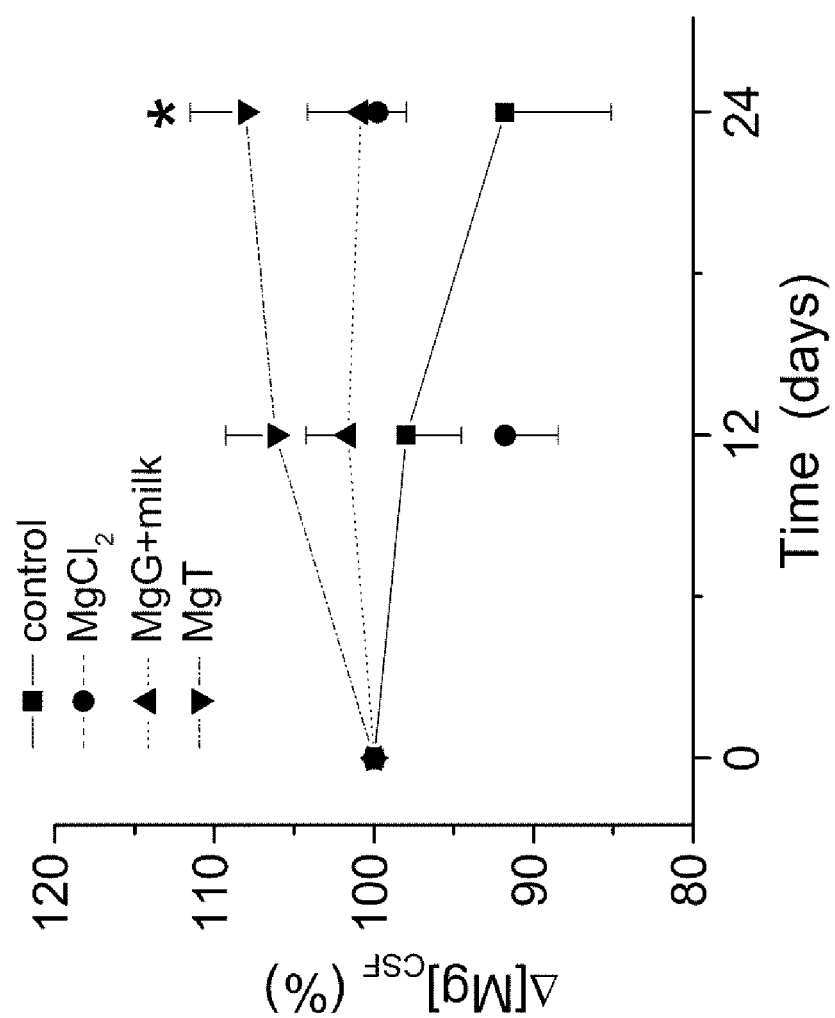
FIG. 3 illustrates a plot of the elevation of magnesium concentration in cerebrospinal fluid ($[M^{2+}]_{CSF}$) following treatment with different preparations. The y-axis shows the change in $[Mg^{2+}]_{CSF}$ and the x-axis represents time in days. The magnesium compounds were magnesium chloride ($MgCl_2$); magnesium gluconate in milk (MgG+milk); and magnesium threonate (MgT).

The high bioavailability of magnesium threonate compared to other forms of magnesium is shown in FIGS. 2A and B. For example, magnesium oxide, the most widely available magnesium supplement, has been reported to have a bioavailability of only 4% (Ranade V V, Somberg J C. Bioavailability and pharmacokinetics of magnesium after administration of magnesium salts to humans. Am J. Ther. 2001 September-October; 8:345-57). Thus, taking a similarly recommended amount of elemental magnesium using magnesium threonate in long-term may expose a subject to a much higher blood magnesium level previously unattainable with other magnesium supplements. Magnesium threonate also provides superior magnesium retention in the body. FIGS. 2C and D show that, although magnesium threonate has the highest magnesium absorption rate, its rate of blood magnesium excretion through urine is similar to other magnesium compounds. As a result, the rate of magnesium retention (absorption rate−excretion rate), which measures the ultimate bioavailability of a magnesium compound, is higher for magnesium threonate than for other magnesium compounds. Accordingly, this makes magnesium threonate by far the most efficient compound to elevate magnesium levels in tissues and other body fluids. Indeed, magnesium threonate increased brain magnesium level (i.e., magnesium concentration in cerebral spinal fluid (CSF)) significantly in mice following 24 days of treatment, whereas magnesium chloride and magnesium gluconate in milk had relatively limited effect (FIG. 3). These data indicate that threonate is unusually capable of facilitating magnesium to enter the brain. This rise of brain magnesium coincided with the animals' cognitive function improvement. See U.S. patent application Ser. No. 12/054,373, entitled "Magnesium Compositions, Methods of Using Same, and Associated Technology."

Accordingly, the present invention provides a method of elevating magnesium in a central nervous system of a subject comprising administering to said subject an oral dosage form as described herein. In some embodiments, the oral dosage form comprises a controlled-release form of magnesium (Mg) and threonate (T), wherein said threonate comprises one or more of a threonate salt or a threonate precursor. In some embodiments, administering the oral dosage form provides an increased concentration of magnesium in a cerebral spinal fluid of the subject, wherein said increased concentration of magnesium in said cerebral spinal fluid of the subject ranges between about a 5% increase to about a 10% increase after about 10 days compared to baseline in the absence of administering magnesium. In some embodiments, the increased concentration of magnesium in said cerebral spinal fluid ranges between about a 1% to about a 10% increase, or about a 2% to about a 10% increase, or about a 3% to about a 10% increase, or about a 4% increase to about a 10% increase after about 10 days administering said oral dosage form. In some embodiments, said increased concentration of magnesium in said cerebral spinal fluid of the subject is increased by more than about 1%, 2%, 3%, 4%, 5%, 6%, 7%, 8%, 9%, or more than about a 10% increase after about 10 days.

Figure 4:
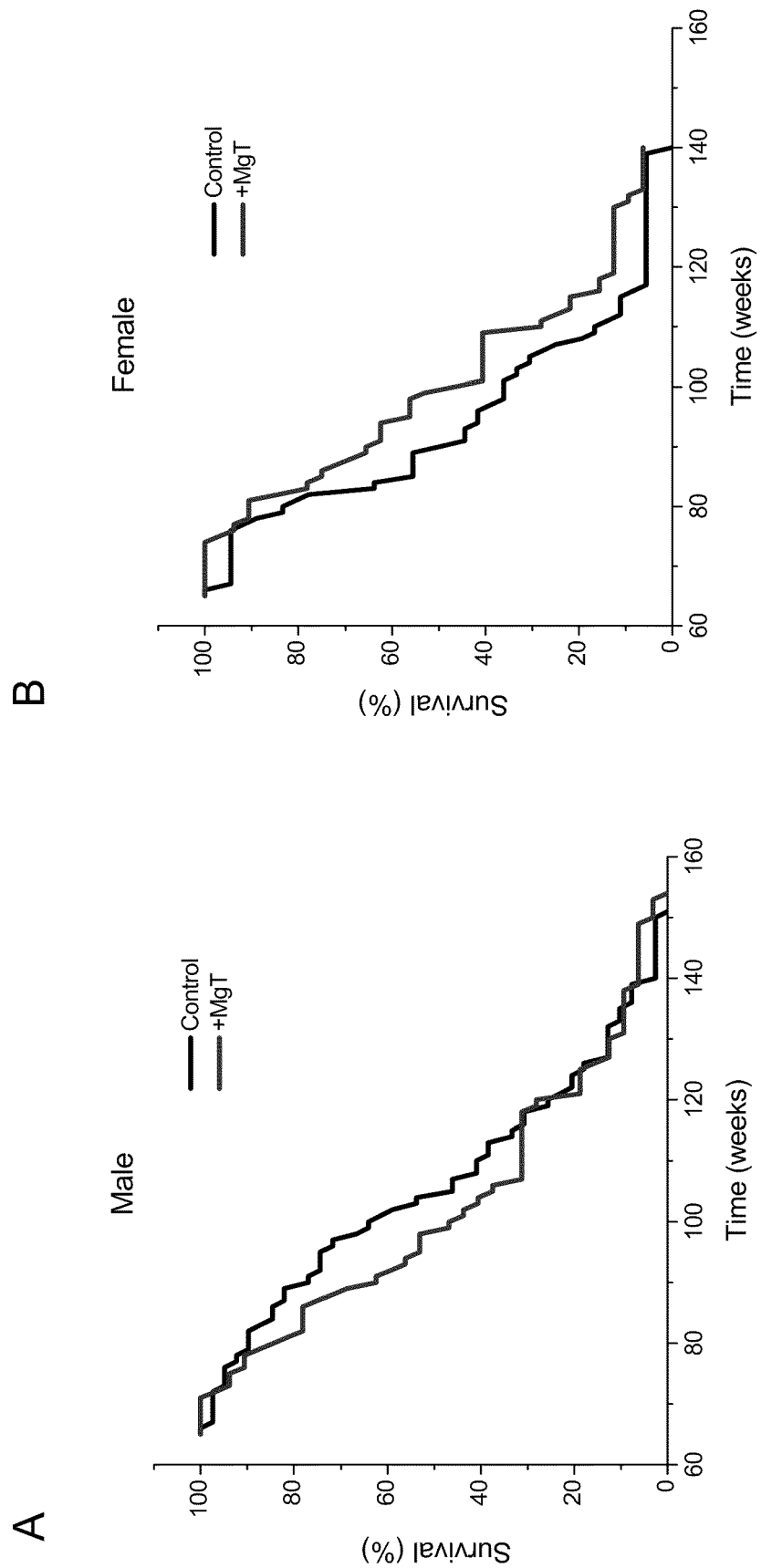
FIG. 4A illustrates survival curves for male mice with and without magnesium threonate (MgT) supplementation.
FIG. 4B illustrates survival curves of female mice with and without MgT supplementation.

The compositions of the present invention are able to provide such high levels of magnesium without adverse effect. In some embodiments, the compositions are provided with adverse effect for at least 1 month, 2 months, 3 months, 4 months, 5 months, or for at least 6 months. In some embodiments, the compositions are provided with adverse effect for at least 1 year, or 2 years, or 5 years, or 20 years, or 20 years, or for a lifetime. For example, normal male and female mice at age 15 months were treated with magnesium threonate for their remaining entire lifespan. See I.Example 4. The results show that the magnesium-treated animals had normal lifespan (FIG. 4). In these experiments, the amount of magnesium daily dosage (75 mg/kg/day) corresponded to the effective dosage for memory enhancement in normal young and aging mice as well as in AD mice in the short-term magnesium treatment experiments. See U.S. patent application Ser. No. 12/054,373, "Magnesium Compositions, Methods of Using Same, and Associated Technology." The data indicate that magnesium threonate has no long-term toxicity in animals when used at a physiologically effective dosage.

Figure 5:
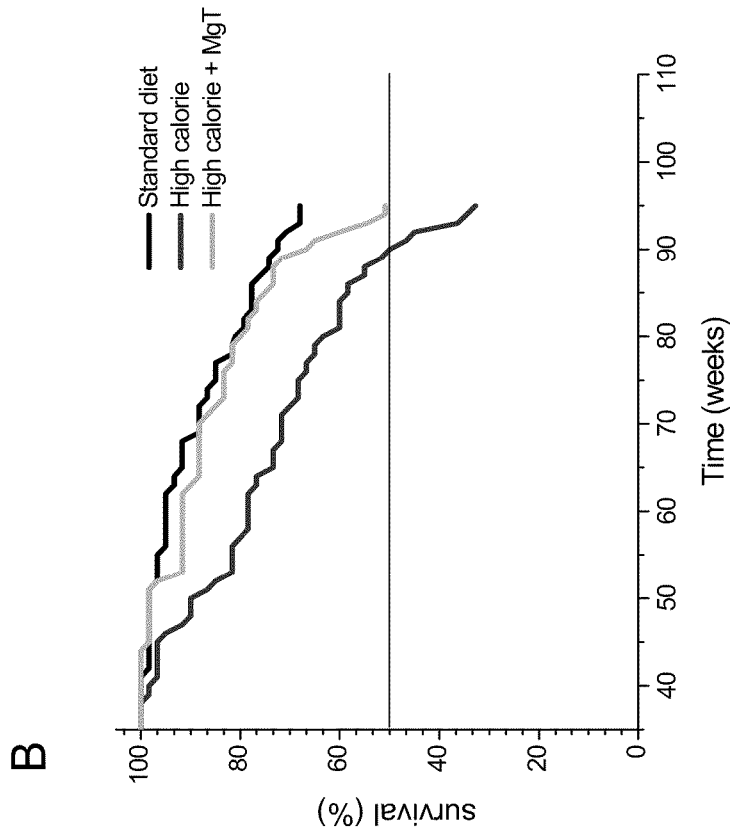
FIG. 5A illustrates the body weight of mice fed a standard or high calorie (HC) diet over time.
FIG. 5B illustrates survival curves of mice under standard or high calorie diet. Mice under high calorie diet have shorter life span than the mice under standard diet. Mice under high calorie diet plus MgT had life span similar to mice under standard diet.
Figure 5:
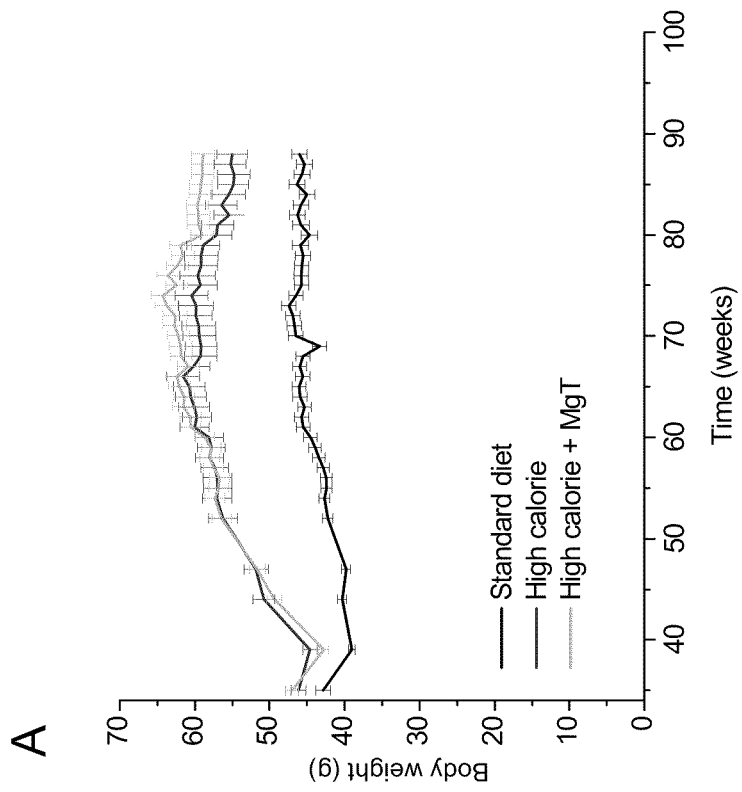

The oral dosage forms of the present invention further provide protective health benefits against a high calorie diet. In an experiment, the compound was given to 10-month old mice on a high calorie diet throughout the remaining lifespan. As expected, the group of animals under high calorie diet plus magnesium threonate and another group of animals under high calorie diet but without magnesium threonate (control group #1) both gained significant weight over time (FIG. 5A). Also as expected, the animals in the high calorie control group (control group #1) died at a much higher rate than animals fed standard mouse diet (control group #2) (FIG. 5B). However, the animals under high calorie diet plus magnesium threonate had lifespan similar to that of the animals under standard diet. It is generally well-known that a high calorie diet may lead to obesity, which in turn can lead to a variety of health problems including diabetes and cardiovascular diseases. The results in FIG. 5 suggest that magnesium threonate may have preventative effect to metabolic syndrome and other health problems associated with obesity, thus making the compound useful for general health-enhancing purpose in addition to its use as a magnesium supplement.

A number of serious complications can result from obesity. These include type II diabetes, unhealthy cholesterol levels, heart disease (e.g., atherosclerosis, myocardial infarction, congestive heart failure, thromboembolism, sudden cardiac death, angina or chest pain), stroke, high blood pressure, sleep apnea, breathing disorders, musculoskeletal disorders (e.g., osteoarthritis, back pain), gall bladder disease, fatty liver disease, cancer, asthma, chronic headaches, varicose veins, deep vein thrombosis, coronary artery disease, gastroesophageal reflux disease (GERD), heartburn, depression, hernias, gall stones, urinary incontinence, menstrual irregularity, infertility, and increased pregnancy risk for both mother and child. Obesity leads to numerous premature deaths.

In one embodiment, the present invention provides a method of maintaining a high calorie diet without a substantial risk of high calorie related adverse effect, comprising administering an oral dosage form as described herein to a subject. In one embodiment, the oral dosage form comprises magnesium (Mg) and threonate (T), wherein the threonate comprises one or more of a threonate salt or a threonate precursor. The oral dosage form is effective in increasing the life span of a subject on a high calorie diet. In some embodiments, administering said oral dosage form to a subject on a high calorie diet yields a protective effect such that said subject's life span is comparable to an average life span of a subject having a median weight.

In one embodiment, the invention provides an oral dosage form comprising magnesium (Mg) and threonate (T), wherein said threonate comprises one or more of a threonate salt or a threonate precursor, wherein administering said oral dosage form to a subject provides protection against adverse effects of a high calorie diet in said subject. Adverse effects include, but are not limited to, artherosclerosis, heart disease, myocardial infarction, stroke, thromboembolism, metabolic syndrome, and diabetes. A variety of other complications resulting from obesity are disclosed herein.

The health beneficial effects of the compounds of the present invention can be measured in test animals, e.g., rodents, e.g., mice or rats. See I.Example 5. In some embodiments, the oral dosage form increases survival rate by at least about 10%, 20%, 30%, 40%, 50%, or more than 50% in such animals who are on a high calorie diet for at least about 60 weeks. In some embodiments, the increased survival rate is observable over shorter time periods. In some embodiments, the oral dosage form increases survival rate by a statistically significant amount in such animals who are on a high calorie diet for at least about 10 weeks, 20 weeks, 30 weeks, 40 weeks, or for at least about 50 weeks. One of skill in the art will appreciate how to measure survival effects, e.g., using a Kaplan-Meier survival curve analysis.

III. Kits

The present invention also provides kids that can be used to practice the present invention. A kit may comprise at least one component of any magnesium-counter ion composition described herein or any magnesium-counter ion composition described herein. In some embodiments, a kit comprises magnesium-threonate supplements, or any of the variations described herein, in a controlled-release oral dosage form. In some embodiments, a kit contains a bottle or other holder containing said oral dosage form. In some embodiments, the oral dosage forms are comprised in blister packs to simplify health and therapeutic regimen for end users.

EXAMPLES

Example 1

Methods

Animals: Adult male Sprague-Dawley rats were obtained from Wei Tong Li Hua Beijing, China. Rats were individually-housed with free access to standard food and water under a 12:12 h reversed light-dark cycle, with light onset at 8:00 p.m. On arrival and before the start of the bioavailability experiments (see below), rats were fed a commercial pelleted diet, containing normal magnesium (0.15%) and tap water ad lib. All experimental procedures were approved by the Tsinghua University Committees on Animal Care.

Treatment with different Magnesium preparations: The following magnesium preparations were used in the present study, Magnesium threonate (Magceutics Inc., USA), Magnesium chloride and glycinate (Modern Eastern Fine Chemical, China), magnesium gluconate and citrate (Sigma-Aldrich, Germany). Lactose was obtained from Biobasic Inc (Beijing, China). In order to supply animals with a dose of 50 mg/kg/day elemental magnesium the following doses of each preparation were dissolved in the daily drinking volume: magnesium threonate (606 mg/kg/day), magnesium chloride (196 mg/kg/day), magnesium gluconate (853 mg/kg/day), magnesium citrate (310 mg/kg/day), and magnesium glycinate (355 mg/kg/day).

Determination of magnesium absorption, excretion and retention: Rats were individually-housed in metabolic cages for 12 days, during which time the animals received magnesium-free food. On day 4 through day 10, animals received de-ionized water containing one of the tested magnesium compounds. From day 11 through day 12, the rats were fed with magnesium-free food and de-ionized water. Urine from each rat was collected daily during the magnesium supplement period (days 4 to 10), and fecal pellets were collected from day 5 to day 10. The collected urine and fecal pellets were pooled and the total volume of the pooled urine and total weight of feces from each rat were recorded. The pooled urine and fecal pellets from each rat were analyzed for magnesium content using an inductively coupled plasma-atomic emission spectrometer (ICP-AES), and the total magnesium content (milligrams) in urine and feces was determined.

The percentages of absorption, excretion, and retention were estimated by the slope of the linear regression fit using the following equations:

$$\text{absorption} = (Mg_{intake} - Mg_{feces}) * 100\% / Mg_{intake} \quad \text{(Equation 1)}$$

$$\text{excretion} = Mg_{urine} * 100\% / (Mg_{intake} - Mg_{feces}) \quad \text{(Equation 2)}$$

$$\text{retention} = (Mg_{intake} - Mg_{feces} - Mg_{urine}) * 100\% / Mg_{intake} \quad \text{(Equation 3)}$$

Margin of safety of different magnesium preparations: To evaluate the laxative properties of different magnesium preparations, animals were divided into groups of 10. Each group received the specified magnesium preparation via drinking water at a dose ranging from 15 to 138 mg/kg/day elemental magnesium. The magnesium dose dissolved in the daily intake volume of water was determined based on intake of ~30 ml/day/rat. Animals were supplied with the magnesium supplemented drinking water for 4 days, after which time the number of animals that developed diarrhea was monitored and calculated as a percentage of the total number of animals in the respective group.

Magnesium content in the cerebrospinal fluid: In a separate group of animals, the content of magnesium ion in cerebrospinal fluid (CSF) was estimated at baseline (day 0), and at 12 and 24 days of treatment with different magnesium preparations. Animals were treated with different magnesium preparations via drinking water at a dose of approximately 50 mg/kg/day elemental magnesium. Before each sampling point, rats were anesthetized with Chloral hydrate (400 mg/kg, i.p.) and 50 μl/animal CSF was manually obtained from the cisterna magna by the interruption of the atlanto-occipital membrane using a micro-needle having a 450 μm diameter. The CSF samples were collected and stored at −20° C. until the magnesium measurements were performed. Magnesium levels were determined as described above.

Statistical analysis: All data were approximated with a normal distribution. Bioavailability analyses were performed using linear regression with 95% confidence-interval. To determine the toxic dose for 50% of the animals (TD50), non-linear regression best-fit with variable Hill-slope analyses was used with a confidence interval of 95%. One-way analysis of variance was used to analyze the cerebrospinal fluid data. GraphPad prism was used for data analysis (version 5.00, GraphPad software Inc.). P-values less than 0.05 were considered significant.

Example 2

Effect of Magnesium Supplementation on the Incidence of Diarrhea

FIG. 1 shows the incidence of diarrhea in rats fed a variety of magnesium supplements. As the magnesium dose was increased, the percentage of animals that developed diarrhea increased proportionally. At higher doses, magnesium threonate (MgT) was less likely to induce diarrhea. TD50 (toxic dose required to induce diarrhea in 50% of animals) of each compound was as follow: magnesium threonate: 131.5 mg/kg/day; magnesium gluconate in milk (MgG+milk): 119.1 mg/kg/day; magnesium gluconate (MgG): 99.7 mg/kg/day; magnesium chloride (MgCl2): 90.0 mg/kg/day. Magnesium compounds were added to the rats drinking water, thereby mimicking slow release of Magnesium compounds as the rats drink over time.

Example 3

Elevation of Magnesium Concentration in Cerebrospinal Fluid ($[Mg^{2+}]CSF$)

Magnesium chloride ($MgCl_2$), magnesium gluconate in milk (MgG+milk), and magnesium threonate (MgT) were fed to mice for 24 days. FIG. 3 shows the elevation of magnesium concentration in cerebrospinal fluid ($[Mg^{2+}]CSF$) following treatment with the different magnesium preparations. Magnesium threonate increased magnesium concentration in cerebral spinal fluid significantly in mice following 24 days of treatment, whereas magnesium chloride and magnesium gluconate in milk had relatively limited effect. The data were significant at day 24 using a one-way ANOVA ($p<0.05$).

Example 4

Effect of Magnesium Threonate (MgT) on the Lifespan of Animals Fed Normal Food Male and female mice at 10 months of age were purchased from the Vital River Laboratory Animal Technology Co. Ltd Beijing, China. The mice were fed a commercial pelleted diet (Shanghai SLAC Laboratory Animal Co. Ltd), containing normal magnesium (0.15%) and tap water ad lib for 5 months prior to the start of the experiment. Four female mice were housed together in single cage with free access to food and water under a 12:12 h light-dark cycle, with light onset at 8:00 a.m. Male mice were housed individually. At the start of the experiment, magnesium threonate (75 mg/kg/day elemental magnesium) was added to drinking water for mice as indicated. Survival curves were plotted using the Kaplan-Meier method, which includes all available animals at each time point. 30 mice were used in each group at the start of experiments (FIGS. 4A and B).

Example 5

Effect of Magnesium Threonate (MgT) on the Lifespan of Animals Fed a High Calorie Diet Female mice at 9 months of age were purchased from the Vital River Laboratory Animal Technology Co. Ltd Beijing, China. The mice were fed on a commercial pelleted diet (Shanghai SLAC Laboratory Animal Co. Ltd), containing normal magnesium (0.15%) and tap water ad lib for one month prior to the start of the experiment. Four mice were housed together in single cage with free access to food and water under a 12:12 h light-dark cycle, with light onset at 8:00 a.m. At the start of experiment, a portion of the mice were switched to a high-calorie (HC) diet by the addition of hydrogenated coconut oil to provide 60% of calories from fat (Baur et al., 2006 Resveratrol improves health and survival of mice on a high-calorie diet. Nature 444, 337-342). A portion of the HC-fed mice were supplemented with MgT supplement via their drinking water at approximately 45 mg/kg/day elemental magnesium. Food intake and body weight were measured on a weekly basis for the duration of the study. Survival curves were plotted using the Kaplan-Meier method, which includes all available animals at each time point. 60 mice were used in each group (i.e., normal diet, HC diet, HC diet with MgT supplementation) at the start of experiments (FIGS. 5A and B).

Example 6

Preparation and Release Profile of Controlled-Release Tablets

To prepare controlled release tablets, magnesium threonate was pulverized and screen filtered using 80 mesh sieves. The magnesium threonate powder was mixed with 15% polyvinylpyrrolidone (PVP) in 95% ethanol at 0.3 mL for each gram of magnesium threonate powder. The resulting particles were screen filtered to remove any un-bound magnesium threonate using 12-mesh sieves. The particles were dried with forced air at 65° C. for 15 minutes, followed by screen filtration again to remove any unbound debris using 12-mesh sieves. A pharmaceutically acceptable amount of magnesium stearate was added to the dried particles as a lubricant (~5 mg for each gram of magnesium threonate). After thorough mixing, the lubricated particles were compressed into tablets of ~1 g in size. A coating liquid was prepared by mixing 223.67 g of 30% SR 30D (polyvinyl acetate) in water, 6.7 g of propylene glycol and 19 g of PVP, followed by adding water to a total weight of 450 g. A pharmaceutically suitable amount of a lake dye and talc powder or titanium oxide were also added to provide protection from light and facilitate the coating process. The resulting mixture was well stirred to form a homogeneous suspension. The tablets were coated at 45-55° C. using the above coating liquid, resulting in controlled-release tablets each comprising ~1 g of magnesium threonate and 70-90 mg of additives.

The release profile of the controlled-release tablets prepared above was examined in 250 mL normal saline at 37° C. at a stirring rate of 75 rpm. The amount of released magnesium over time was measured using a spectroscopic method (Raymond J. Liedtke and Gery Kroon Clin. Chem. 30(11), 1801-1804 (1984)). The release profile is shown in Table 1.

TABLE 1

Released magnesium over time

| Time (h) | % of released magnesium |
|---|---|
| 2 | 0 |
| 4 | 6.9 |
| 6 | 32.5 |
| 8 | 60.1 |
| 10 | 76.2 |
| 12 | 83.3 |
| 24 | 104.6 |

The above data is plotted in FIG. 6B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral dosage form that is a solid or semi-solid comprising magnesium (Mg) and threonate (T), wherein at least a portion of said magnesium (Mg) and threonate (T) are complexed in a salt form of $MgT_2$, wherein said oral dosage form has an in vitro dissolution profile in a dissolution medium, and wherein said dissolution profile ranges between less than or equal to 5% in about 2 hours, less than 10% in about 4 hours, less than 40% in about 6 hours, greater than or equal to 60% in about 10 hours, and greater than or equal to 80% in about 12 hours as measured using a USP type II paddle dissolution system at 75 rpm, at a temperature of 37° C.

2. The oral dosage form of claim 1, wherein said magnesium and threonate in said oral dose form are encapsulated in a tablet.

3. The oral dosage form of claim 1, wherein element magnesium (Mg) is present in an amount equal to at least about 10 mg by weight.

4. The oral dosage form of claim 1, wherein element magnesium (Mg) is present in an amount equal to at least about 20 mg by weight.

5. The oral dosage form of claim 1, wherein said magnesium (Mg) is present in an amount greater than about 1% by weight.

6. The oral dosage form of claim 1, further comprising one or more antioxidants selected from the group consisting of resveratrol, ellagic acid, quercetin, lipoic acid and vitamin C.

7. The oral dosage form of claim 1, wherein said dissolution profile ranges between less than 5% in about 2 hours, less than 10% in about 4 hours, less than 40% in about 6 hours, greater than or equal to 60% in about 10 hours, and greater than or equal to 80% in about 12 hours as measured using a USP type II paddle dissolution system at 75 rpm, at a temperature of 37° C.

8. The oral dosage form of claim 1, wherein 75% to 100% of said magnesium (Mg) and threonate (T) in said oral dose form are provided in a controlled release dosage form.

9. An oral dosage form that is a solid or semi-solid comprising between about 10 mg to 500 mg elemental magnesium (Mg), wherein said oral dosage form is a controlled release formulation, and wherein administering said oral dosage form to a Sprague-Dawley rat at a dosage of about 75 mg/kg/day yields an incidence of diarrhea of less than 20%, and wherein at least a portion of said magnesium (Mg) is complexed with threonate (T) in a salt form of $MgT_2$.

10. The oral dosage form of claim 9, wherein the incidence of diarrhea is less than 20% when administered at a dosage of about 75 mg/kg/day for at least about 3 days.

11. The oral dosage form of claim 9, wherein said oral dosage form yields an incidence of diarrhea of less than 20% when administered at a dosage of about 75 mg/kg/day in Sprague-Dawley rats and yields an incidence of diarrhea of less than 50% when administered at a dosage of about 130 mg/kg/day in Sprague-Dawley rats.

12. The oral dosage form of claim 1, wherein said oral dosage form is administered to a human subject at a dose between about 1 mg elemental magnesium/kg/day to about 16 mg elemental magnesium/kg/day.

13. An oral dosage form that is a solid or semi-solid comprising magnesium (Mg) and threonate (T), wherein at least a portion of said magnesium (Mg) and threonate (T) are complexed in a salt form of $MgT_2$, wherein upon administering said oral dosage form to a subject at least about 50% of said administered magnesium is absorbed in said subject, or that at least 30% of the magnesium administered to the subject is retained by the subject over a period of at least two days when said oral dosage form is administered at a dose of 20 mg/kg/day or higher.

14. A method of treating a magnesium deficient condition comprising administering a subject in need thereof an oral dosage form of any of claims 1, 9, and 13.

* * * * *

UNITED STATES PATENT AND TRADEMARK OFFICE
CERTIFICATE OF CORRECTION

PATENT NO. : 8,377,473 B2
APPLICATION NO. : 12/829361
DATED : February 19, 2013
INVENTOR(S) : Guosong Liu et al.

Page 1 of 1

It is certified that error appears in the above-identified patent and that said Letters Patent is hereby corrected as shown below:

In the Claims

Column 48, Claim 14, line 33, replace "administering a subject" with --administering to a subject--.

Signed and Sealed this
Seventeenth Day of December, 2013

Margaret A. Focarino
*Commissioner for Patents of the United States Patent and Trademark Office*